(12) United States Patent
Durack

(10) Patent No.: US 8,778,279 B2
(45) Date of Patent: Jul. 15, 2014

(54) MICROFLUIDIC DEVICE

(75) Inventor: Gary P. Durack, Urbana, IL (US)

(73) Assignees: Sony Corporation, Tokyo (JP); Sony Corporation of America, New York, NY (US)

( * ) Notice: Subject to any disclaimer, the term of this patent is extended or adjusted under 35 U.S.C. 154(b) by 360 days.

(21) Appl. No.: 12/831,138

(22) Filed: Jul. 6, 2010

(65) Prior Publication Data

US 2011/0003325 A1    Jan. 6, 2011

Related U.S. Application Data

(60) Provisional application No. 61/223,089, filed on Jul. 6, 2009, provisional application No. 61/233,090, filed on Jul. 6, 2009, provisional application No. 61/223,091, filed on Jul. 6, 2009, provisional application No. 61/223,399, filed on Jul. 7, 2009, provisional application No. 61/223,400, filed on Jul. 7, 2009, provisional application No. 61/233,401, filed on Jul. 7, 2009, provisional application No. 61/223,094, filed on Jul. 6, 2009, provisional application No. 61/223,402, filed on Jul. 7, 2009, provisional application No. 61/223,404, filed on Jul. 7, 2009.

(51) Int. Cl.
*B01L 3/00*     (2006.01)

(52) U.S. Cl.
USPC ....... 422/502; 422/52; 422/82.05; 422/82.06; 422/82.07; 422/82.08; 422/82.09; 422/82.11; 422/407; 422/501; 422/503; 436/164; 436/165; 436/172; 436/174; 436/518; 436/805; 436/809; 435/164; 435/165; 435/283.1; 435/287.1; 435/287.2; 435/288.7; 435/808; 435/4; 435/5; 435/7.2; 435/7.9

(58) Field of Classification Search
CPC ............. G01N 1/34; G01N 15/0205; B01L 2200/027; B01L 2200/0652; C12M 23/16
USPC ............ 422/52, 82.05, 82.06, 82.07, 82.08, 422/82.09, 82.11, 407, 501, 502, 503; 435/164, 165, 283.1, 287.1, 287.2, 435/288.7, 808, 4, 5, 7.2, 7.9; 436/164, 436/165, 172, 174, 518, 805, 809; 204/403.01; 506/3, 39; 359/321; 250/458.1, 559.29, 574; 356/128, 244, 356/246, 300, 326, 414, 416, 445; 430/290, 430/321
See application file for complete search history.

(56) References Cited

U.S. PATENT DOCUMENTS 3,526,219 A   9/1970   Balamuth
3,814,098 A   6/1974   Deaton
3,861,877 A   1/1975   Matharani et al.
(Continued)

FOREIGN PATENT DOCUMENTS

WO    WO 02/40978 A2      5/2002
WO    WO 2008/019448 A1   2/2008

OTHER PUBLICATIONS

International Search Report and Written Opinion issued in PCT/US2010/040923, mailed Aug. 30, 2010.

(Continued)

*Primary Examiner* — Dennis M White
(74) *Attorney, Agent, or Firm* — Ice Miller LLP

(57) ABSTRACT

The present disclosure relates to microfluidic devices adapted for facilitating cytometry analysis of particles flowing therethrough. In certain embodiments, the microfluidic devices have onboard sterilization capabilities. In other embodiments, microfluidic devices have integral collection bags and methods for keeping the microfluidic channels clean.

10 Claims, 14 Drawing Sheets

(56) References Cited

U.S. PATENT DOCUMENTS

| | | | |
|---|---|---|---|
| 4,256,405 | A | 3/1981 | Fjarlie |
| 4,465,488 | A | 8/1984 | Richmond |
| 4,867,908 | A | 9/1989 | Recktenwald et al. |
| 5,157,465 | A | 10/1992 | Kronberg |
| 5,315,122 | A | 5/1994 | Pinsky et al. |
| 5,466,572 | A | 11/1995 | Sasaki et al. |
| 5,478,722 | A | 12/1995 | Caldwell |
| 5,726,751 | A | 3/1998 | Altendorf et al. |
| 5,793,485 | A | 8/1998 | Gourley |
| 6,245,508 | B1 | 6/2001 | Heller et al. |
| 6,268,219 | B1 | 7/2001 | McBride et al. |
| 6,280,960 | B1 | 8/2001 | Carr |
| 6,632,399 | B1 | 10/2003 | Kellogg et al. |
| 6,877,528 | B2 | 4/2005 | Gilbert et al. |
| 6,900,021 | B1 | 5/2005 | Harrison et al. |
| 7,214,298 | B2 | 5/2007 | Spence et al. |
| 7,351,376 | B1 | 4/2008 | Quake et al. |
| 2002/0005354 | A1 | 1/2002 | Spence et al. |
| 2002/0173033 | A1 | 11/2002 | Hammerick et al. |
| 2003/0054558 | A1 | 3/2003 | Kurabayashi et al. |
| 2004/0219662 | A1 | 11/2004 | Geiger |
| 2004/0224380 | A1 | 11/2004 | Chou et al. |
| 2005/0006238 | A1 | 1/2005 | Jaffe |
| 2005/0009060 | A1 | 1/2005 | Beernink et al. |
| 2005/0105077 | A1 | 5/2005 | Padmanabhan et al. |
| 2005/0112541 | A1 | 5/2005 | Durack et al. |
| 2005/0260175 | A1 | 11/2005 | Hedrick et al. |
| 2006/0011478 | A1 | 1/2006 | Fouillet et al. |
| 2006/0024756 | A1 | 2/2006 | Tibbe et al. |
| 2006/0134003 | A1 | 6/2006 | Georgakoudi et al. |
| 2006/0194264 | A1 | 8/2006 | Sheppard et al. |
| 2006/0281143 | A1 | 12/2006 | Liu et al. |
| 2007/0095669 | A1 | 5/2007 | Lau et al. |
| 2007/0183934 | A1 | 8/2007 | Diercks et al. |
| 2007/0190525 | A1 | 8/2007 | Gu et al. |
| 2007/0215528 | A1 | 9/2007 | Hayenga et al. |
| 2007/0240495 | A1 | 10/2007 | Hirahara |
| 2007/0263477 | A1 | 11/2007 | Sudarsan et al. |
| 2008/0003690 | A1 | 1/2008 | Chow |
| 2008/0047836 | A1 | 2/2008 | Strand et al. |
| 2008/0072663 | A1 | 3/2008 | Keenan et al. |
| 2008/0107386 | A1 | 5/2008 | Kudou et al. |
| 2008/0176211 | A1 | 7/2008 | Spence et al. |
| 2008/0213915 | A1 | 9/2008 | Durack et al. |
| 2008/0300148 | A1 | 12/2008 | Lee et al. |
| 2009/0027666 | A1 | 1/2009 | Godin et al. |
| 2009/0051912 | A1 | 2/2009 | Salazar et al. |
| 2009/0053686 | A1 | 2/2009 | Ward et al. |
| 2009/0054529 | A1 | 2/2009 | Neas et al. |
| 2009/0081688 | A1 | 3/2009 | Luo et al. |
| 2009/0195852 | A1 | 8/2009 | Bassler et al. |

OTHER PUBLICATIONS

International Search Report and Written Opinion Issued in PCT/US2010/041058, mailed Sep. 7, 2010.

International Search Report and Written Opinion issued in PCT/US2010/041062, mailed Aug. 20, 2010.

International Search Report and Written Opinion issued in PCT/US2010/041067, mailed Sep. 22, 2010.

International Search Report and Written Opinion issued in PCT/US2010/041094, mailed Sep. 2, 2010.

Nederlof et al. Multiple Fluorescence in situ hybridization; Cytometry, 1990, vol. 11, Iss. 1, pp. 126-131.

International Search Report and Written Opinion issued in PCT/US2010/041087, mailed Oct. 26, 2010.

International Search Report and Written Opinion Issued in PCT/US2010/041090, mailed Oct. 13, 2010.

Kang et al. Technical Paper on Microfluidic Devices Cell Separation Technology, Paper, Dec. 2005.

Tsutsui et al. Cell Separation by Non-Inertial Force Fields in Microfluidic Systems; Manuscript, Jan. 1, 2009.

MICROFLUIDIC DEVICE

CROSS-REFERENCE TO RELATED APPLICATIONS

The present application claims the benefit of the following: U.S. Provisional Patent Application No. 61/223,089, which was filed Jul. 6, 2009, U.S. Provisional Patent Application No. 61/223,090, which was filed Jul. 6, 2009, U.S. Provisional Patent Application No. 61/223,091, which was filed Jul. 6, 2009, U.S. Provisional Patent Application No. 61/223,399, which was filed Jul. 7, 2009, U.S. Provisional Patent Application No. 61/223,400, which was filed Jul. 7, 2009, U.S. Provisional Patent Application No. 61/223,401, which was filed Jul. 7, 2009, U.S. Provisional Patent Application No. 61/223,094, which was filed Jul. 6, 2009, U.S. Provisional Patent Application No. 61/223,402, which was filed Jul. 7, 2009, U.S. Provisional Patent Application No. 61/223,404, which was filed Jul. 7, 2009, all of which are hereby incorporated herein by reference in their entireties.

TECHNICAL FIELD OF THE DISCLOSURE

The present disclosure relates to microfluidic cytometry systems.

BACKGROUND OF THE DISCLOSURE

Flow cytometry-based cell sorting was first introduced to the research community more than 20 years ago. It is a technology that has been widely applied in many areas of life science research, serving as a critical tool for those working in fields such as genetics, immunology, molecular biology and environmental science. Unlike bulk cell separation techniques such as immuno-panning or magnetic column separation, flow cytometry-based cell sorting instruments measure, classify and then sort individual cells or particles serially at rates of several thousand cells per second or higher. This rapid "one-by-one" processing of single cells has made flow cytometry a unique and valuable tool for extracting highly pure sub-populations of cells from otherwise heterogeneous cell suspensions.

Cells targeted for sorting are usually labeled in some manner with a fluorescent material. The fluorescent probes bound to a cell emit fluorescent light as the cell passes through a tightly focused, high intensity, light beam (typically a laser beam). A computer records emission intensities for each cell. These data are then used to classify each cell for specific sorting operations. Flow cytometry-based cell sorting has been successfully applied to hundreds of cell types, cell constituents and microorganisms, as well as many types of inorganic particles of comparable size.

Flow cytometers are also applied widely for rapidly analyzing heterogeneous cell suspensions to identify constituent sub-populations. Examples of the many applications where flow cytometry cell sorting is finding use include isolation of rare populations of immune system cells for AIDS research, isolation of genetically atypical cells for cancer research, isolation of specific chromosomes for genetic studies, and isolation of various species of microorganisms for environmental studies. For example, fluorescently labeled monoclonal antibodies are often used as "markers" to identify immune cells such as T lymphocytes and B lymphocytes, clinical laboratories routinely use this technology to count the number of "CD4 positive" T cells in HIV infected patients, and they also use this technology to identify cells associated with a variety of leukemia and lymphoma cancers.

Recently, two areas of interest are moving cell sorting towards clinical, patient care applications, rather than strictly research applications. First is the move away from chemical pharmaceutical development to the development of biopharmaceuticals. For example, the majority of novel cancer therapies are now biologics containing proteins or peptides. These include a class of antibody-based cancer therapeutics. Cytometry-based cell sorters can play a vital role in the identification, development, purification and, ultimately, production of these products.

There is also a move toward the use of cell replacement therapy for patient care. Much of the current interest in stem cells revolves around a new area of medicine often referred to as regenerative therapy or regenerative medicine. These therapies may often require that large numbers of relatively rare cells be isolated from sample patient tissue. For example, adult stem cells may be isolated from bone marrow or adipose tissue and ultimately used as part of a re-infusion back into the patient from whom they were removed. Cytometry lends itself very well to such therapies.

There are two basic types of cell sorters in wide use today. They are the "droplet cell sorter" and the "fluid switching cell sorter." The droplet cell sorter utilizes micro-droplets as containers to transport selected cells to a collection vessel. The micro-droplets are formed by coupling ultrasonic energy to a jetting stream. Droplets containing cells selected for sorting are then electrostatically steered to the desired location. This is a very efficient process, allowing as many as 90,000 cells per second to be sorted from a single stream, limited primarily by the frequency of droplet generation and the time required for illumination.

A detailed description of a prior art flow cytometry system is given in United States Published Patent Application No. US 2005/0112541 A1 to Durack et al.

Droplet cell sorters, however, are not particularly biosafe. Aerosols generated as part of the droplet formation process can carry biohazardous materials. Because of this, biosafe droplet cell sorters have been developed that are contained within a biosafety cabinet so that they may operate within an essentially closed environment. Unfortunately, this type of system does not lend itself to the sterility and operator protection required for routine sorting of patient samples in a clinical environment.

The second type of flow cytometry-based cell sorter is the fluid switching cell sorter. Most fluid switching cell sorters utilize a piezoelectric device to drive a mechanical system which diverts a segment of the flowing sample stream into a collection vessel. Compared to droplet cell sorters, fluid switching cell sorters have a lower maximum cell sorting rate due to the cycle time of the mechanical system used to divert the sample stream. This cycle time, the time between initial sample diversion and when stable non-sorted flow is restored, is typically significantly greater than the period of a droplet generator on a droplet cell sorter. This longer cycle time limits fluid switching cell sorters to processing rates of several hundred cells per second. For the same reason, the stream segment switched by a fluid cell sorter is usually at least ten times the volume of a single micro-drop from a droplet generator. This results in a correspondingly lower concentration of cells in the fluid switching sorter's collection vessel as compared to a droplet sorter's collection vessel.

Newer generation microfluidics technologies offer great promise for improving the efficiency of fluid switching devices and providing cell sorting capability on a chip similar in concept to an electronic integrated circuit. Many microfluidic systems have been demonstrated that can successfully sort cells from heterogeneous cell populations. They have the advantages of being completely self-contained, easy to sterilize, and can be manufactured on sufficient scales (with the resulting manufacturing efficiencies) to be considered a disposable part.

A generic microfluidic device is illustrated in FIG. 1 and indicated generally at 10. The microfluidic device 10 comprises a substrate 12 having a fluid flow channel 14 formed therein by any convenient process as is known in the art. The substrate 12 may be formed from glass, plastic or any other convenient material, and may be substantially transparent or substantially transparent in a portion thereof. In certain embodiments, the substrate 12 is injection molded. In certain embodiments, the substrate 12 comprises industrial plastic such as a Cyclo Olefin Polymer (COP) material, or other plastic. As a result, the substrate 12 is transparent such that a cytometry optics module can analyze the sample fluid stream as described further below. In one embodiment, the microfluidic device 10 is disposable.

The substrate 12 further has three ports 16, 18 and 20 coupled thereto. Port 16 is an inlet port for a sheath fluid. Port 16 has a central axial passage that is in fluid communication with a fluid flow channel 22 that joins fluid flow channel 14 such that sheath fluid entering port 16 from an external supply (not shown) will enter fluid flow channel 22 and then flow into fluid flow channel 14. The sheath fluid supply may be attached to the port 16 by any convenient coupling mechanism as is known to those skilled in the art. In one embodiment, the sheath fluid comprises a buffer or buffered solution. For example, the sheath fluid comprises 0.96% Dulbecco's phosphate buffered saline (w/v), 0.1% BSA (w/v), in water at a pH of about 7.0.

Port 18 also has a central axial passage that is in fluid communication with a fluid flow channel 14 through a sample injection tube 24. Sample injection tube 24 is positioned to be coaxial with the longitudinal axis of the fluid flow channel 14. Injection of a liquid sample of cells into port 18 while sheath fluid is being injected into port 16 will therefore result in the cells flowing through fluid flow channel 14 surrounded by the sheath fluid. The dimensions and configuration of the fluid flow channels 14 and 22, as well as the sample injection tube 24 are chosen so that the sheath/sample fluid will exhibit laminar flow as it travels through the device 10, as is known in the art. Port 20 is coupled to the terminal end of the fluid flow channel 14 so that the sheath/sample fluid may be removed from the microfluidic device 10.

While the sheath/sample fluid is flowing through the fluid flow channel 14, it may be analyzed using cytometry techniques by shining an illumination source through the substrate 12 and into the fluid flow channel 14 at some point between the sample injection tube 24 and the outlet port 20. Additionally, the microfluidic device 10 could be modified to provide for a cell sorting operation, as is known in the art.

Although basic microfluidic devices similar to that described hereinabove have been demonstrated to work well, there is a need in the prior art for improvements to cytometry systems employing microfluidic devices. The present invention is directed to meeting this need.

SUMMARY OF THE DISCLOSURE

The present disclosure relates to microfluidic devices adapted for facilitating cytometry analysis of particles flowing therethrough. In certain embodiments, the microfluidic devices have onboard sterilization capabilities. In other embodiments, microfluidic devices have integral collection bags and methods for keeping the microfluidic channels clean.

In one embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, a sterilization repository onboard said substrate, said sterilization repository being fluidically coupled to said flow channel, and a substance disposed in said sterilization repository, said substance being operative to sterilize said flow channel when said substance flows from said sterilization repository into said flow channel.

In another embodiment, a method of detecting particles in a sample is disclosed, the method comprising the steps of: a) providing a microfluidic device, said microfluidic device comprising: a substrate, a flow channel formed in said substrate for transport of a liquid sample, a sterilization repository onboard said substrate, said sterilization repository being fluidically coupled to said flow channel, a sterilizing substance disposed within said sterilization repository, and a valve disposed between said sterilization repository and said flow channel; b) flowing said sample through said flow channel; and c) opening said valve such that said sterilizing substance contained in said sterilization repository may flow through said flow channel, thereby sterilizing said flow channel.

In another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, said flow channel having an outlet, and a collection bag coupled to said substrate and having an inlet fluidically coupled to said flow channel outlet.

In yet another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, said flow channel having an outlet and a collection bag coupled to said substrate and having an inlet fluidically coupled to said flow channel outlet, wherein said collection bag comprises an inner bag fluidically coupled to said inlet, and an outer bag enclosing said inner bag.

In yet another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, said flow channel having an outlet and a collection bag coupled to said substrate and having an inlet fluidically coupled to said flow channel outlet, wherein said collection bag comprises an artificial insemination straw.

In yet another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, said flow channel having an outlet, a well onboard said substrate and fluidically coupled to said flow channel, said well having a porous surface, and a collection bag coupled to said substrate and having an inlet fluidically coupled to said porous surface.

In still another embodiment, a method of detecting particles in a sample is disclosed, the method comprising the steps of: a) providing a microfluidic device, said microfluidic device comprising: a substrate, an input port, a flow channel formed in said substrate for transport of a liquid sample, said flow channel fluidically coupled to said input port, and an output port fluidically coupled to said flow channel; b) flowing said sample through said flow channel; c) attaching a collection bag to said output port; d) allowing sample to flow from said flow channel and into said collection bag; e) after step (d), detaching said collection bag from said output port; and f) after step (e), attaching said collection bag to said input port.

In another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, said flow channel having an outlet, a sheath fluid flow channel formed in said substrate and fluidically coupled to said microfluidic flow channel, and a collection bag having a first chamber and a second chamber, said first chamber being fluidically coupled to said microfluidic flow channel outlet and said second chamber being fluidically coupled to said sheath fluid flow channel.

In yet another embodiment, a microfluidic device is disclosed, comprising a substrate, a sheath fluid flow channel formed in said substrate, wherein said flow channel extends through a portion of said substrate adapted to facilitate cytometry analysis of cells flowing in said flow channel, said flow channel having an outlet, a microfluidic flow channel formed in said substrate and having an outlet nozzle, and wherein said microfluidic flow channel intersects said sheath fluid flow channel such that said outlet nozzle is positioned to inject said cells substantially in a center of said sheath fluid flow channel.

In still another embodiment, a method of detecting particles in a sample is disclosed, the method comprising the steps of: a) providing a microfluidic device, said microfluidic device comprising: a substrate, an input port, a flow channel formed in said substrate for transport of a liquid sample, said flow channel fluidically coupled to said input port, and an output port fluidically coupled to said flow channel; b) mixing a detergent and a cell sample to create a mixture; and c) flowing said mixture through said flow channel.

Other embodiments are also disclosed.

DESCRIPTION OF THE ILLUSTRATED EMBODIMENTS

Figure 1:
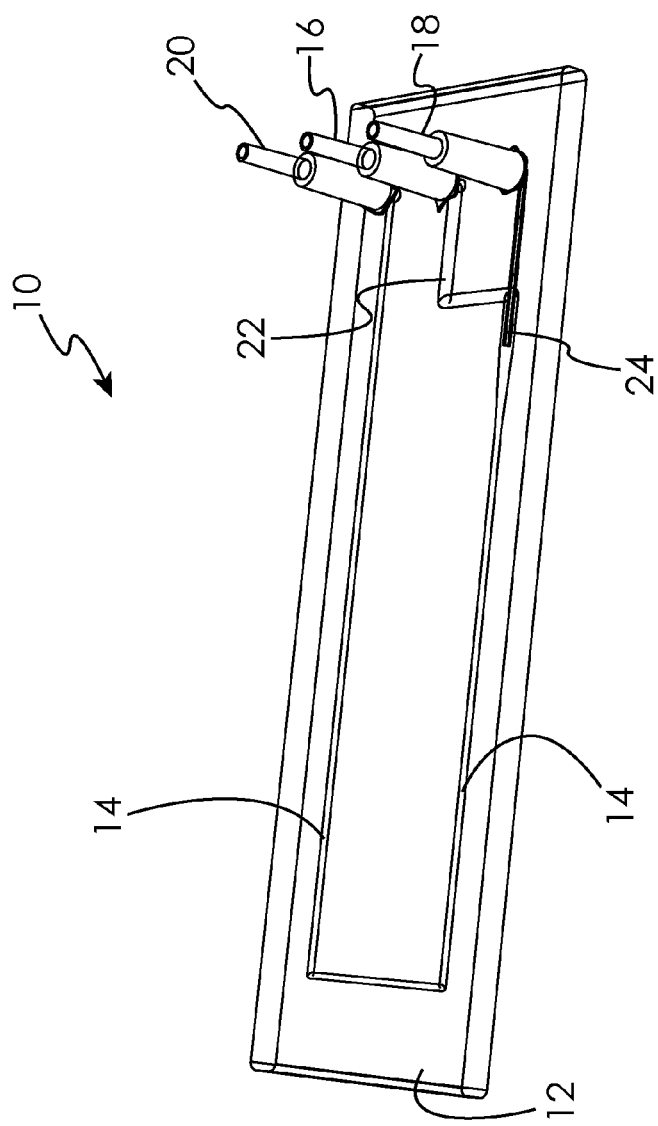
FIG. 1 is a perspective view of a prior art microfluidic device.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein are contemplated as would normally occur to one skilled in the art to which the disclosure relates.

Microfluidic Device Having Onboard Sterilization Capability

Certain embodiments of the present disclosure are generally directed to integral sterilization capabilities on a microfluidic device, such as a cytometry chip, to sterilize the device after the cell sample undergoes the cytometry analysis. The cytometry analysis may be a flow cytometry analysis, as described above, or an image cytometry analysis. In certain embodiments, the integral sterilization capabilities include a sterilizing or inactivating fluid contained on the device and allowing the fluid, such as inactivating reagent, to flood the components of the device after the analysis is complete to sterilize the device of any dangerous or harmful cell or tissue sample thereon. For example, after the cytometry analysis of a blood sample as part of an AIDS test, it is desirable to sterilize the device after use.

Figure 2:
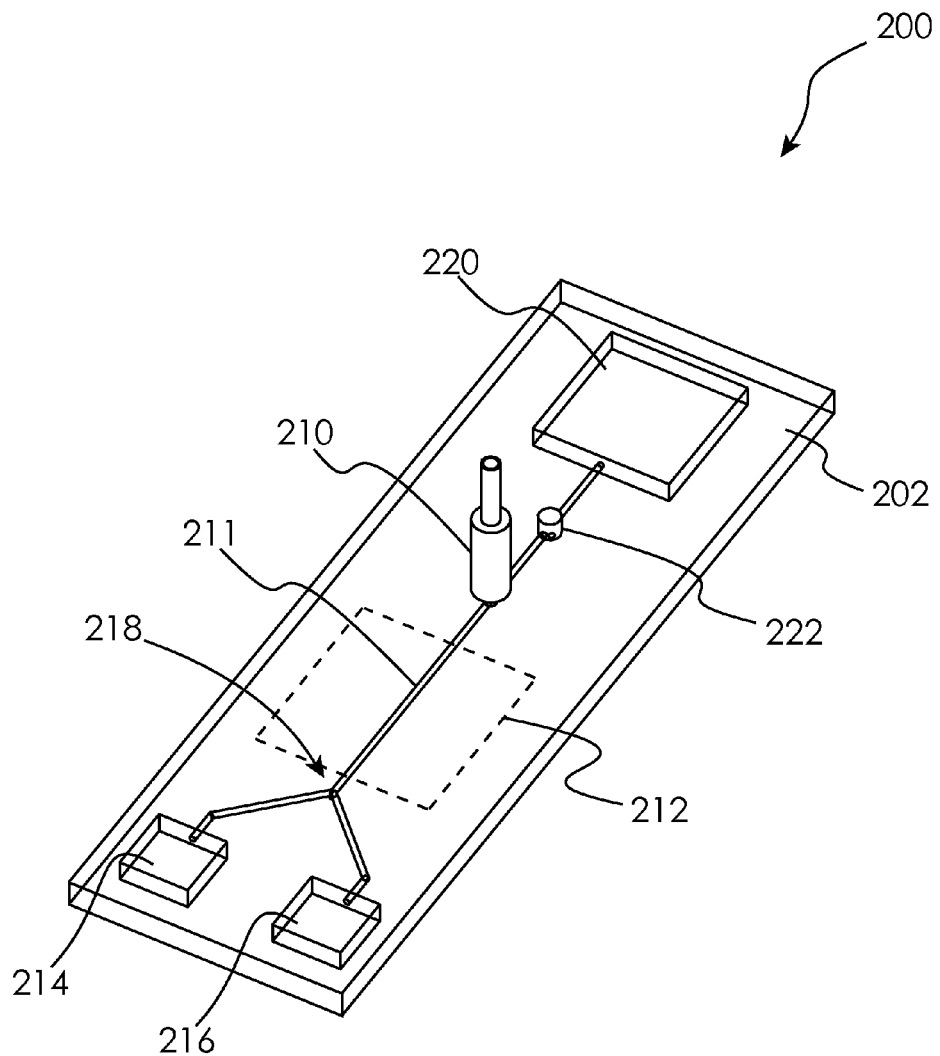
FIG. 2 is a schematic perspective view of a microfluidic device according to an embodiment of the present disclosure.

FIG. 2 illustrates a microfluidic device 200 comprising a substrate 202. Cells from an external cell supply (not shown) are introduced into the microfluidic device via port 210 and are carried by flow channel 211. Optionally, an additional port to introduce a supply of sheath fluid may be added, as discussed hereinabove with respect to FIG. 1. Cells within flow channel 211 are analyzed via cytometry in analysis section 212 (the specific operations that occur in analysis section 212 are not critical to the present disclosure). According to the results of the analysis performed, the cells may optionally be sorted into different chambers 214 and 216 formed in the substrate 202 based on differing characteristics of the cells. The chip may include a flow diverter 218 for physically diverting the cells into the chambers 214, 216 from the analysis section 212 as is known in the art. In certain embodiments, the sample wells 214, 216 have outlet ports (not shown) in fluid communication therewith in order to facilitate removal of the sorted sample from the wells. Alternatively, the cells may be caused to exit the chip 200 after the analysis is complete without being directed to a storage well. For simplicity and ease of illustration, FIG. 2 shows single channels extending between the components, areas or sections of chip 200. However, it should be appreciated that the single channels may be representative of multiple cytometry channels and a variety of possible configurations of channels as would occur to one skilled in the art.

In one embodiment, the flow diverter 218 is a piezoelectric device that can be actuated with an electric command signal in order to mechanically divert the flow through the sorting channel 211 into either the well 214 or the well 216, depending upon the position of the flow diverter 218. In other embodiments, flow diverter 218 is not a piezoelectric device, but instead can be, for example, an air bubble inserted from the wall to deflect the flow, a fluid deflector moved or actuated by a magnetic field or any other flow diverter or sorting gate as would occur to one of ordinary skill in the art.

Cells may be sorted into different wells or chambers based on the intended future use for the cells. For example, cells having the same characteristics, or phenotype, may be sorted into one well where they are fixed for viewing, and sorted into another well where they are maintained in a viable state to undergo additional functional measurements. Alternatively, the cells may be deposited into the wells or chambers based on volume as opposed to a sorting method.

The microfluidic device 200 may contain an inactivating fluid in a sterilization repository 220 for sterilization of the device 200. After the cells are analyzed in section 210 and optionally sorted into various chambers, the inactivating fluid may be allowed to flow out of sterilization repository 220 and travel through the components of chip 200 to sterilize the components. In the particular illustrated embodiment, the inactivating fluid may be released from repository 220 by opening the valve 222, flow to port 210, flow through analysis section 212 in the flow channel 211, and flow into optional chambers 214, 216. However, it should be appreciated that the flow of the inactivating fluid may occur in a different configuration or arrangement as would occur to one skilled in the art. To that end, the sterilization repository 220 is shown as being positioned near the top of the chip; however, it should be appreciated that the repository may be positioned elsewhere on the chip.

The inactivating fluid contained within repository 220 and used to sterilize the device may be any appropriate inactivating fluid as would occur to one skilled in the art. As one example, the inactivating fluid may be a suitable concentration of sodium hypochlorite. Containing the inactivating fluid within the repository 220 on the device 200 eliminates (or reduces) the need for interaction with an external sterilizing apparatus to sterilize the microfluidic device after use. This is particularly useful for uses in environments where Biohazard Disposal is not routine, such as field work in developing countries where standard laboratory disposal is not readily available.

Release of the inactivating fluid from sterilization repository 220 may be accomplished by manual operation by a user of the chip 200 (i.e. manual operation of the valve 222). Alternatively, release of the inactivating fluid may be accomplished under control of the device performing the cytometry analysis 212, such as by having the device performing the cytometry analysis open the valve 222 maintaining the inactivating fluid within the sterilization repository 220. Means for activation of such valves are well known in the art. In another embodiment, the valve 222 may be a plug in the flow channel 211 that is dissolved when a predetermined liquid is input into the port 210 and reacts with the material forming the plug, thereby allowing the contents of the sterilization repository 220 to flow therefrom.

Figure 3A:
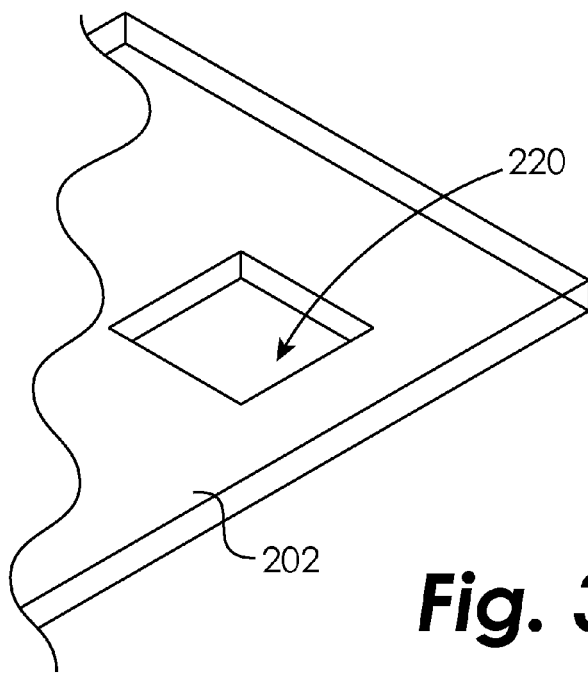
FIGS. 3A-D are schematic perspective views of exemplary means for forming a sterilization repository on a microfluidic device.
Figure 3B:
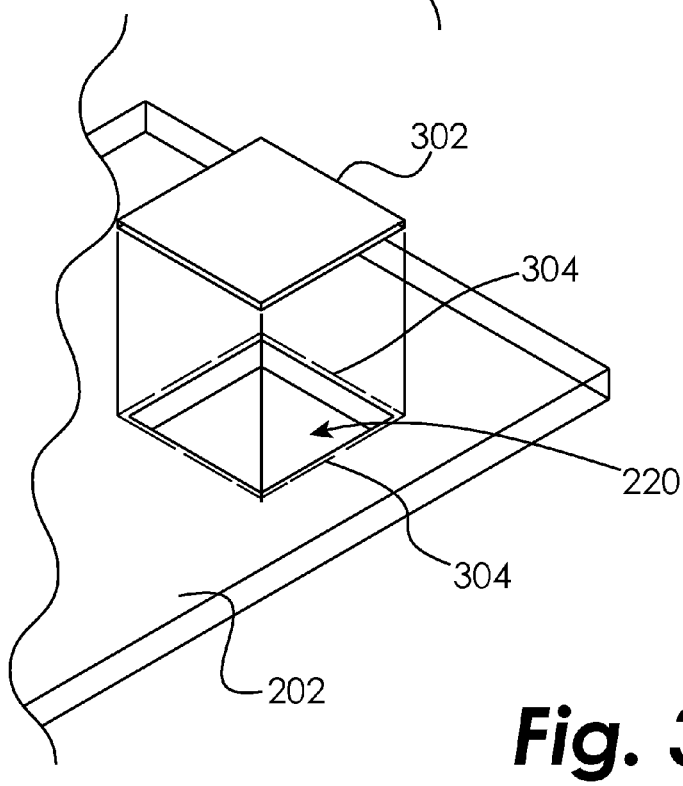
Figure 3C:
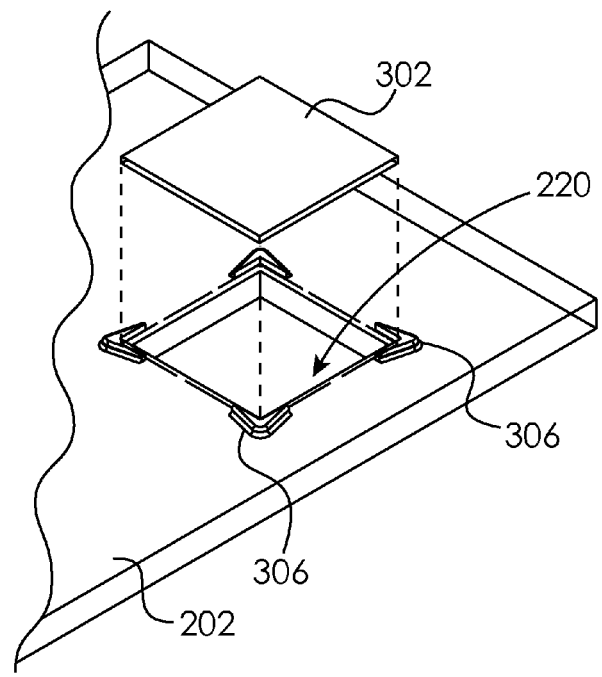
Figure 3D:
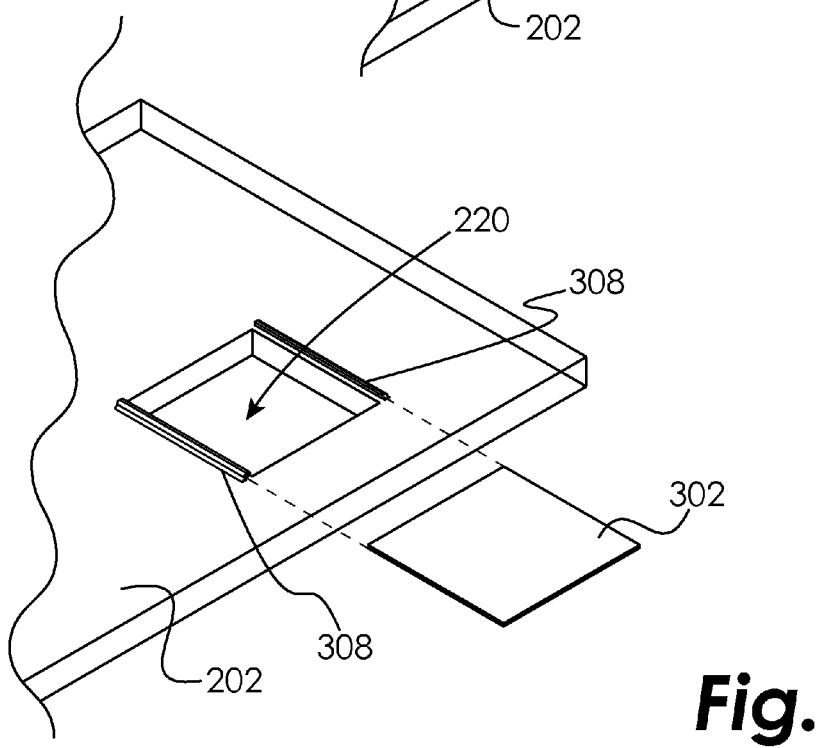

As shown in FIGS. 3A-D, the sterilization repository 220 may take any convenient physical form, such as an open well 220 formed into the surface of the substrate 202, which may remain open as shown in FIG. 3A. In certain embodiments, the sample repository 220 may include a cover 302 that is glued in place by means of an adhesive 304 placed on the surface of the substrate 202. In certain embodiments, the adhesive 304 is placed upon the surface of the substrate 202 when it is manufactured and is covered by a release layer that may be removed prior to adhering the cover 302 to the substrate 202, as illustrated in FIG. 3B. In other embodiments, the cover 302 may be snapped in place with resilient members 306 that engage the substrate 202 and provide an interference fit when the cover 302 is snapped into place, as illustrated in FIG. 3C. In other embodiments, the cover 302 may be slid into place under guides 308 that extend from the substrate 202 surface, as illustrated in FIG. 3D. The examples of FIGS. 3A-D are given by way of non-limiting example only, and the present disclosure comprehends any other convenient means as would occur to one of ordinary skill in the art. The above examples are intended to be only non-limiting examples of many possible configurations.

In an alternative embodiment, sterilization or inactivation can be done by providing a mechanism which immerses the chip 200 in an inactivating solution and allowing the inactivating solution to spread through the components of the chip. In such embodiments, the chip may be designed such that a chemical reaction occurs which opens a port to allow the inactivating solution to permeate the chip. Additionally, in another alternative embodiment, the chip 200 may be additionally sterilized or inactivated by exposing the chip to other forms of sterilization, including the application of ultraviolet radiation.

It should be appreciated that use of the term inactivating or inactivation is meant to include either or both of sterilization and inactivation. Additionally, it should be appreciated that use of the term sterilizing or sterilization is meant to include either or both of sterilization and inactivation. Further, use of either term contemplates the result of rendering any human or animal pathogens inactive or unable to infect a living being.

Microfluidic Device Having Sterile Collection Bag

Figure 4:
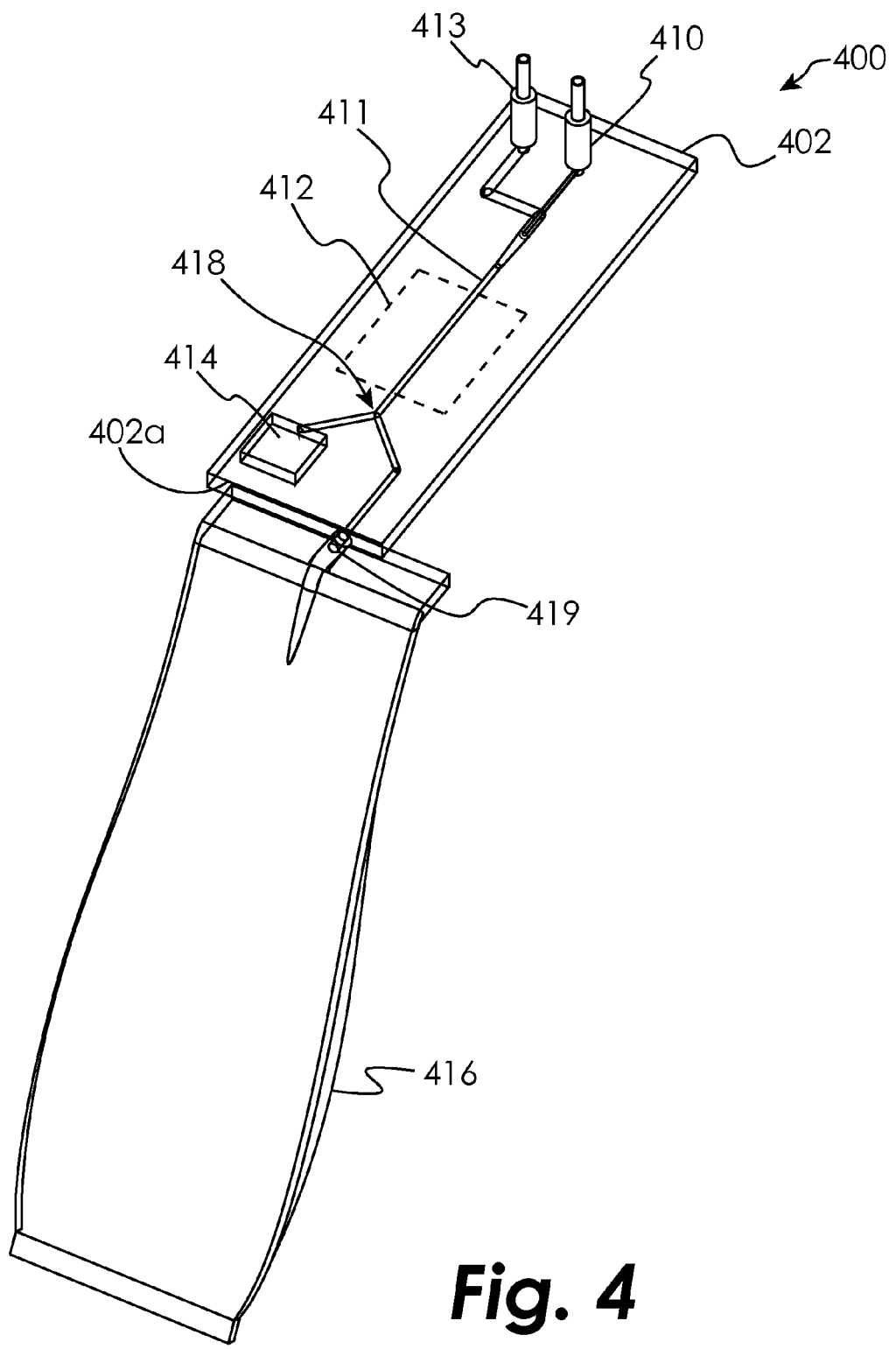
FIG. 4 is a schematic perspective view of a microfluidic device according to an embodiment of the present disclosure.

Certain embodiments of the present disclosure are generally directed to systems for the storage, preservation and transport of cells via a sterile collection bag or container that is integral to a microfluidic device, such as a cytometry chip, the cells being diverted or directed into the bag following the cytometry analysis. In certain embodiments, the cytometry analysis is a flow cytometry analysis or an image cytometry analysis. FIG. 4 illustrates a microfluidic device 400 comprising a substrate 402. Cells from an external cell supply (not shown) are introduced into the microfluidic device via port 410 and are carried by flow channel 411. Optionally, an additional input port 413 to introduce a supply of sheath fluid may be added, as discussed hereinabove with respect to FIG. 1. Cells within flow channel 411 are analyzed via cytometry in analysis section 412 (the specific operations that occur in analysis section 412 are not critical to the present disclosure). According to the results of the analysis performed, the cells may be sorted into one or more different wells or chambers 414 and/or one or more different sterile collection bags 416. The cells collected in the sterile collection bag 416 may be, for example, stored and preserved within the bag for later viewing, imaging or testing by a medical professional and/or may be transported to a different location or delivered to a different process via the sterile collection bag 416.

The chip may include a flow diverter 418 disposed in the flow channel 411 for physically diverting the cells into the chamber 414 or the sterile collection bag 416 from the analysis section 412 as is known in the art. In the illustrated example, after the cells are analyzed in analysis section 412, the cells may be sorted into either chamber 414 or sterile collection bag 416 based on differing characteristics of the cells. Cells may be sorted into the chamber or the bag based on the intended future use for the cells. For example, cells having the same characteristics, or phenotype, may be sorted into the chamber 414 where they are fixed for viewing and sorted into the sterile collection bag 416 where they are maintained in a viable state to undergo additional functional measurements, or properly stored for use as part of a cell-based therapeutic procedure. Alternatively, the cells may be deposited into the chamber 414 and/or the sterile collection bag 416 based on volume as opposed to a sorting method. Chamber 414 may have an output port (not shown) fluidically coupled thereto for withdrawing its contents from the device 400.

In one embodiment, the flow diverter 418 is a piezoelectric device that can be actuated with an electric command signal in order to mechanically divert the flow through the sorting channel 411 into either the well 414 or the sterile collection bag 416, depending upon the position of the flow diverter 418. In other embodiments, flow diverter 418 is not a piezoelectric device, but instead can be, for example, an air bubble inserted from the wall to deflect the flow, a fluid deflector moved or actuated by a magnetic field or any other flow diverter or sorting gate as would occur to one of ordinary skill in the art.

For simplicity, the illustration of FIG. 4 shows a single chamber 414 and a single sterile collection bag 416; however, it should be appreciated that the microfluidic device may include more chambers and/or bags as would occur to one of ordinary skill in the art. In an alternative embodiment, the microfluidic device may only include one or more sterile collection bags 416, with the chamber 414 being absent. Additionally, the sterile collection bag 416 is shown as being positioned extending below the bottom surface 402a of the chip 402; however, it should also be appreciated that the bag 416 may be positioned elsewhere on the chip as would occur to one skilled in the art. Further, the sterile collection bag 416 may occupy a variety of a different shapes and sizes as would occur to one of ordinary skill in the art, with the bag illustrated in FIG. 4 being just one non-limiting example of the numerous possible shapes and sizes.

As in the illustrated embodiment, sterile collection bag 416 may be removably attached to the chip 400 via connection port or member 419. Connection member 419 may be any appropriate connection means as would occur to one of ordinary skill in the art. In other embodiments, the sterile collection bag 416 removably attaches directly to a channel leading from analysis section 412 and thus connection member 419 is absent. Once the analysis at section 412 is complete and the cells have been sorted into either the chamber 414 or the sterile collection bag 416, the sterile collection bag 416 may be detached from chip 400 to transport the cells or may remain attached to the chip 400, either temporarily or permanently, to store the cells for later imaging, viewing, transporting, processing, analysis, use for cell-based therapeutics, or other intended use of the cells. In situations in which the cells are transported via the sterile collection bag 416, the cells may be transported to a storage location or another process or analysis location, as examples. In certain embodiments, the top of the sterile collection bag 416 is integrally formed with substrate 402. In certain other embodiments, the sterile collection bag may be removed from the substrate 402 by snapping the two apart along a frangible line formed therein for the purpose.

In some embodiments, the sterile collection bag 416 may contain the necessary nutrients, reagents and/or other chemicals therein to maintain the cells in a healthy, viable state in the sterile collection bag 416, and keep them alive and functional, for an extended period of time. Such cells could then be used for functional or diagnostic testing. These cells could also be easily integrated into a cell-based therapeutic process for treatment of a patient. In another embodiment, the sterile collection bag 416 may contain the necessary reagents and/or other chemicals therein to fix the cells by exposing them to preservative chemicals to maintain the integrity of the cell sample for later observation or testing by a researcher or medical professional. In such a way, the cells' visual appearance or morphology remains substantially in the same state as when they were sorted. This procedure maintains the integrity of the sorted and isolated cells, substantially preventing the cells from breaking down and thus preserving the morphological characteristic(s) of the cells which may have dictated their sorting. In some embodiments, the reagents and/or other chemicals maintain the cells in a natural, viable state so that they can be placed in culture or used for additional functional measurements. In some embodiments, the reagents and/or other chemicals in the sterile collection bag 416 may facilitate preparation of the cells for freezing, such as by freezing the sterile collection bag 416 by placing the bag in an automated cell cryogenic device, as an example. In certain embodiments, the sterile collection bag 416 may be prepackaged with the necessary reagents and/or chemicals therein. In some embodiments, the reagents and/or chemicals in the sterile collection bag 416 may facilitate analysis of genomic information such as DNA sequencing techniques through a variety of polymerase chain reaction (PCR) techniques.

Additionally, in certain embodiments the sterile collection bag 416 may be temperature controlled in a manner as would occur to one of ordinary skill in the art to maintain a healthy, functional environment for the cells and maintain viability of the cells sorted into and isolated within sterile collection bag 416. Further, the temperature to which the sterile collection bag 416 is controlled may vary depending upon the cell characteristics and type of cells collected within sterile collection bag 416.

Microfluidic Device Having Dual Chamber Sterile Collection Bag

Figure 5:
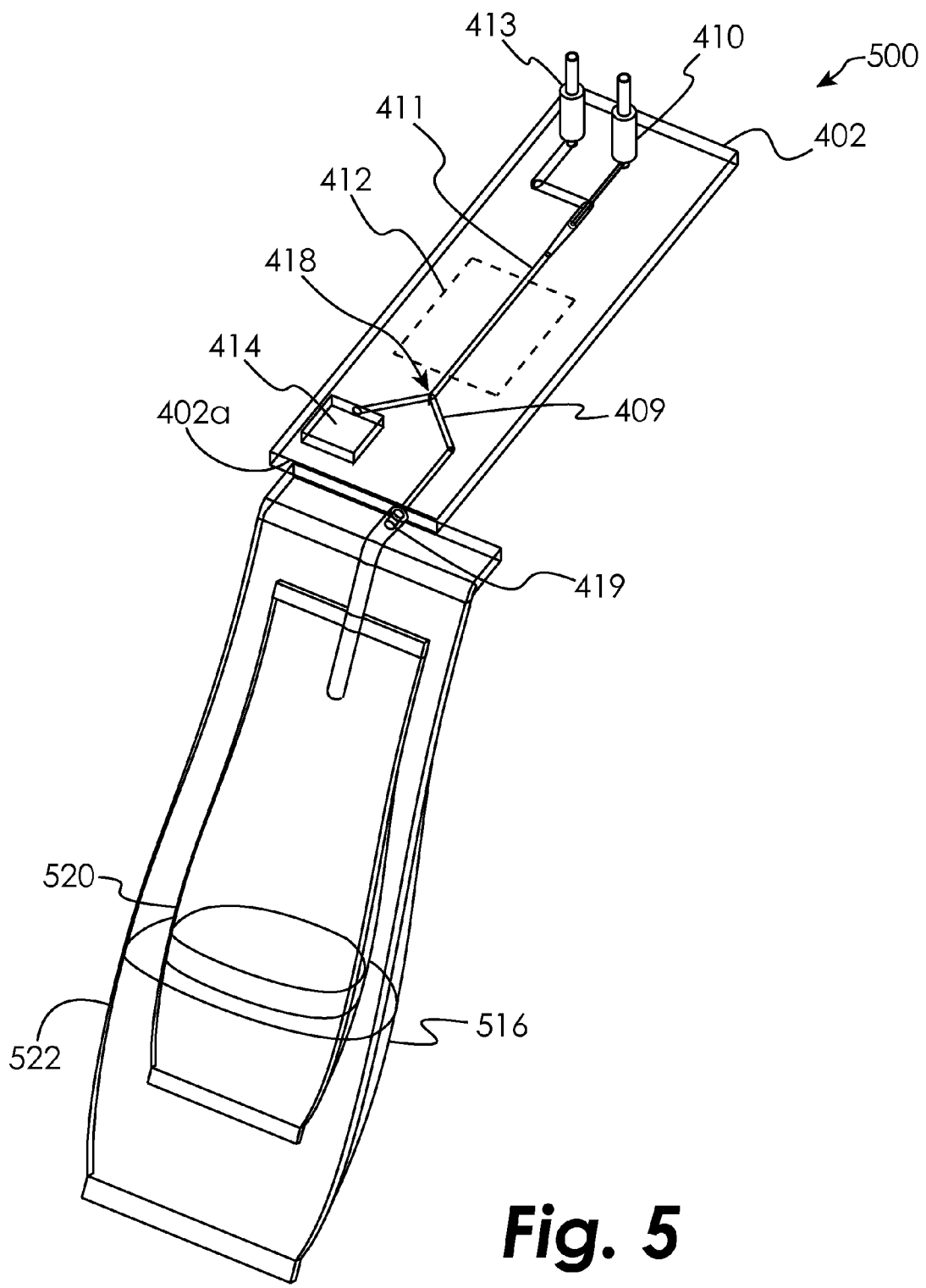
FIG. 5 is a schematic perspective view of a microfluidic device according to an embodiment of the present disclosure.

In certain embodiments, the present disclosure is generally directed to systems for analyzing cells via cytometry, and for the storage, preservation and transport of cells via a dual chamber sterile collection bag on a microfluidic device, such as a cytometry chip, the cells being diverted or directed into the dual chamber bag following the cytometry analysis. In certain embodiments, the cytometry analysis is a flow cytometry analysis or an image cytometry analysis. FIG. 5 illustrates a microfluidic device 500. Except as discussed hereinbelow, the device 500 is substantially similar to the device 400 of FIG. 4, and like reference designators are used to indicate like components.

As illustrated, dual chamber bag 516 is composed of an inner porous bag 520 surrounded by an outer non-porous bag 522. The inner porous bag 520 is sufficiently porous to allow for molecular transport between the bags. In certain embodiments, the inner porous bag 520 serves as a filter for the material entering the dual chamber bag 516. In this way, the alive and functional cells sorted into bag 516 will remain in the inner porous bag 520, while debris such as dead or damaged cells will filter out into outer bag 522 via the porous nature of inner bag 520. Additionally, some, most, or all of the fluid material traveling with the cells will also filter through inner bag 520 into outer bag 522. The filtering of the fluid material may serve to wash the cells and further assist in transferring debris from the inner bag 520 into the outer bag 522. Additionally, the filtering of the fluid material may also serve to provide a higher concentrate of cells within inner bag 520. Higher concentrations of cells can be important in maintaining the integrity and functionality of the cells.

Dual chamber bag 516 may provide nutrients, reagents, and/or other chemicals to the cells sorted into inner bag 520 to feed the cells, keeping them alive and functional, and/or to fix the cells in the bag 520 in their current state for an extended period of time to maintain the integrity of the cell sample for later observation or testing by a medical professional. In such a way, the cells' morphology remains substantially in the same state as when they were sorted. This procedure maintains the integrity of the sorted and isolated cells, substantially preventing the cells from breaking down and thus preserving the morphological characteristic(s) of the cells which may have dictated their sorting. In some embodiments, the nutrients, reagents and/or other chemicals maintain the cells in a natural, viable state so that they can be placed in culture or used for additional functional measurements or used in a cell-based therapeutic procedure. In some embodiments, the nutrients, reagents and/or other chemicals in the bag 516 may facilitate preparation of the cells for freezing, such as by freezing the bag 516 by placing the bag in an automated cell cryogenic device, as an example.

In certain embodiments, the nutrients, reagents, and/or other chemicals may be prepackaged within the inner bag 520 and/or the outer bag 522. In a particular embodiment, the nutrients, reagents, and/or other chemicals may be provided in a dried form, such as a powder, configured to be released within inner bag 520 when the fluid material enters into the bag. Sufficient fluid to initially hydrate or place the reagents in solution may be provided through an additional external port (not shown) or by allowing some flow through the cytometer and into the bag. In other embodiments, the nutrients, reagents, and/or other chemicals can be deposited into outer bag 522 via a tube (not shown) inserted into the bag. In this way, the environment of the inner bag 520 can be adjusted by molecular diffusion to be substantially the same as the environment in the outer bag 522. Reagents added to the outer bag 522 will diffuse into the inner bag 520. Likewise, unwanted molecules such as those created through normal cell metabolism that may be toxic to the cell will diffuse from the inner bag 520 into the outer bag 522.

The inner porous bag 520 may be composed of one or more of a variety of appropriate materials as would occur to one skilled in the art. As an example, inner bag 520 may be composed of 1 micron mesh material capable of molecular transport, similar to the material used for dialysis tubing. As another example, the material may be similar to nitrocellulose filters having an average pore size of 2 microns. As another example, bag 520 may be composed of a porous gel material, such as agarose as an example. In embodiments in which inner bag 520 is formed of agarose material or another appropriate porous gel material, the inner bag 520 can be transported to and directly placed in an environment in which the next process, analysis, or other activity involving attention to the cells is to take place. In said environment, the agarose material can be made to melt, dissolve, or otherwise disintegrate such that the sorted and isolated cells contained within the agarose material forming the inner bag will be released into said environment. In such a way, most or all of the cells will be released into said environment, while losing none (or very few) as would occur via attachment to the material forming the inner bag if a solid material were used. In certain embodiments, the agarose material may be melted or dissolved via the application of heat or the application of one or more substances which react with the agarose to cause it to melt, as is known in the art.

Additionally, in certain embodiments the dual chamber bag 516 may be temperature controlled in a manner as would occur to one of ordinary skill in the art to maintain a healthy, functional environment for the cells and maintain viability of the cells sorted into and isolated within inner bag 520. The inner and outer bags may be controlled at the same or different temperatures. Further, the temperature to which the bags are controlled may vary depending upon the cell characteristics and type of cells collected within inner bag 520.

Figure 6:
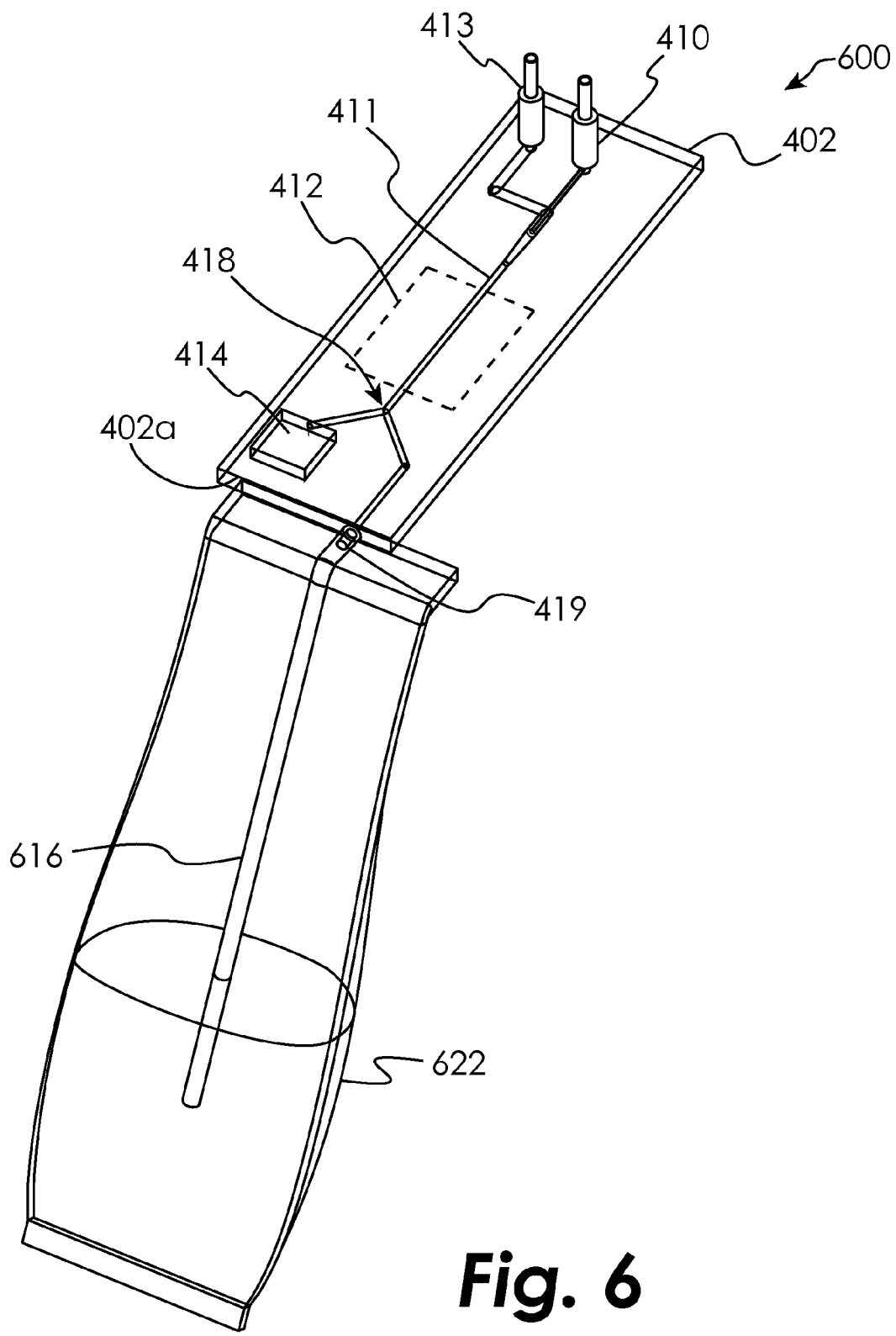
FIG. 6 is a schematic perspective view of a microfluidic device according to an embodiment of the present disclosure.

Microfluidic Device Having Sterile Collection Bag with Artificial Insemination Straw In certain embodiments, the present disclosure is generally directed to systems for analyzing cells, including sperm cells, via cytometry, sorting the cells into a storage and transport device, such as an artificial insemination straw. The cells may be analyzed on a microfluidic device, such as a cytometry chip, some of the cells being diverted or directed into the straw following the cytometry analysis. In certain embodiments, the cytometry analysis is a flow cytometry analysis or an image cytometry analysis. FIG. 6 illustrates a microfluidic device 600. Except as discussed hereinbelow, the device 600 is substantially similar to the device 400 of FIG. 4, and like reference designators are used to indicate like components.

FIG. 6 illustrates a microfluidic device 600 in which cells, including sperm cells, from a cell supply (not shown) are analyzed on the microfluidic device 600 via cytometry in analysis section 412 (the specific operations that occur in analysis section 412 are not critical to the present disclosure). According to the results of the analysis performed, the cells may be sorted into at least one well or chamber 414 and/or at least one straw 616. The cells collected in the straw 616 may be, for example, stored and preserved within the straw via a freezing technique for later use by a researcher or medical professional in an artificial insemination procedure.

In the illustrated example, after the cells are analyzed in analysis section 412, the cells may be sorted into either chamber 414 or straw 616 based on differing characteristics of the cells. Cells may be sorted into the chamber 414 or the straw 616 based on the intended future use for the cells. For example, viable sperm cells may be sorted into straw 616 and all other remaining cells may be sorted into chamber 414. In other embodiments, sperm cells having a desired chromosomal make-up may be sorted into straw 616. Alternatively, the cells may be deposited into the chamber 414 and/or the straw 616 based on volume as opposed to a sorting method.

In certain embodiments, straw 616 may optionally include at least one porous surface to allow for the filtering of dead cells and other debris in the straw. In such cases, the system 600 may optionally include an article to catch or collect the filtered material. As an example, the system may optionally include a non-porous outer bag 622 surrounding straw 616. In certain embodiments, the porous surface of straw 616 is sufficiently porous to allow for molecular transport between the straw 616 and the bag 622. In such a way, the alive and functional sperm cells sorted into straw 616 will remain in the straw 616, while debris such as dead or damaged cells will filter out into outer bag 622 via the porous nature of at least one surface of straw 616. Additionally, in certain embodiments, some, most, or all of the fluid material traveling with the cells will also filter through straw 616 into outer bag 622. The filtering of the fluid material may serve to wash the sperm cells and further assist in transferring debris from the straw 616 into the outer bag 622. Additionally, the filtering of the fluid material may also serve to provide a higher concentrate of sperm cells within straw 616. Higher concentrations of cells can be important in maintaining the integrity and functionality of the cells. Further, in certain embodiments filtering of the fluid material may be necessary to achieve the desired number of cells within the fixed volume of the straw 616. However, it should be appreciated that, in other embodiments, straw 616 does not include a porous surface, no filtering occurs, and outer bag 622 is absent.

Straw 616 may provide nutrients, reagents, and/or other chemicals to the sperm cells sorted into the straw 616 to feed the cells, keeping them alive and functional, and/or to fix the cells in the straw 616 in their current state for an extended period of time to maintain the integrity of the cell sample for later attention by a researcher or medical professional. In certain embodiments, the nutrients, reagents and/or other chemicals in the straw 616 may facilitate preparation of the sperm cells for freezing, such as by freezing the straw 616 by placing the straw in an automated cell cryogenic device, as an example. Additionally, in certain embodiments the straw 616 may be temperature controlled in a manner as would occur to one of ordinary skill in the art to maintain a healthy, functional environment for the cells and maintain viability of the cells sorted into and isolated within the straw 616.

As in the illustrated embodiment, straw 616 (and optional outer bag 622) may be removably attached to the chip 600 via connection port or member 418. Connection member 418 may be any appropriate connection means as would occur to one of ordinary skill in the art. In other embodiments, the straw 616 removably attaches directly to a channel leading from analysis section 412 and thus connection member 418 is absent. Once the analysis at section 412 is complete and the cells have been sorted into either the chamber 414 or the straw 616, the straw 616 may be detached from chip 600 to transport the cells or may remain attached to the chip 600, either temporarily, semi-permanently or permanently, to store the cells for later imaging, viewing, transporting, processing, analysis or other intended use of the cells. As an example, straw 616 containing the sorted sperm cells may be detached from chip 600 and transported to a freezing device, such as a cryogenic freezing machine, to await use in an artificial insemination procedure. In other embodiments, the straw 616 containing the sorted cells may be transported to a storage location or another process or analysis location, as examples.

For simplicity, the illustration of FIG. 6 shows one chamber 414 and one straw 616; however, it should be appreciated that the microfluidic device may include more chambers 414 and/or straws 616 as would occur to one of ordinary skill in the art. In an alternative embodiment, the microfluidic device may only include one or more straws 616, with the cell chamber 414 being absent. Additionally, the straw 616 is shown as extending below the bottom surface 402a of the chip 600; however, it should also be appreciated that the straw 616 may be positioned elsewhere on the chip as would occur to one of ordinary skill in the art. Further, the straw 616 may occupy a variety of a different shapes and sizes as would occur to one of ordinary skill in the art, with the straw illustrated in FIG. 6 being just one non-limiting example of the numerous possible shapes and sizes. Item 616 is referred to herein as a "straw" for simplicity and thus it should be appreciated that item 616 may configured as another appropriate storage and transport device, including another appropriate artificial insemination device as an example.

Microfluidic Device Having Collection Bag with Introduction Port and Waste Port

Figure 7:
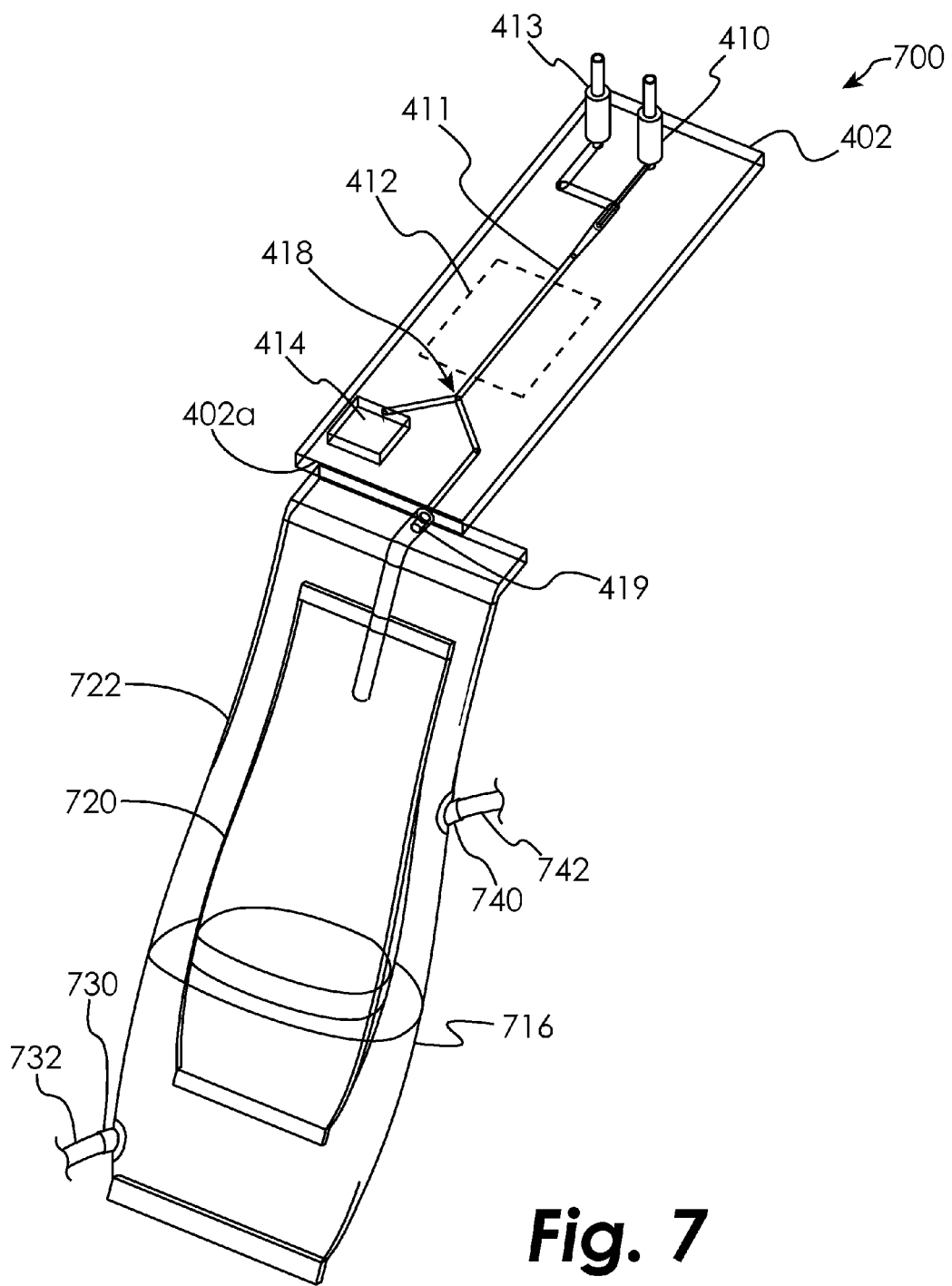
FIG. 7 is a schematic perspective view of a microfluidic device according to an embodiment of the present disclosure.
Figure 8:
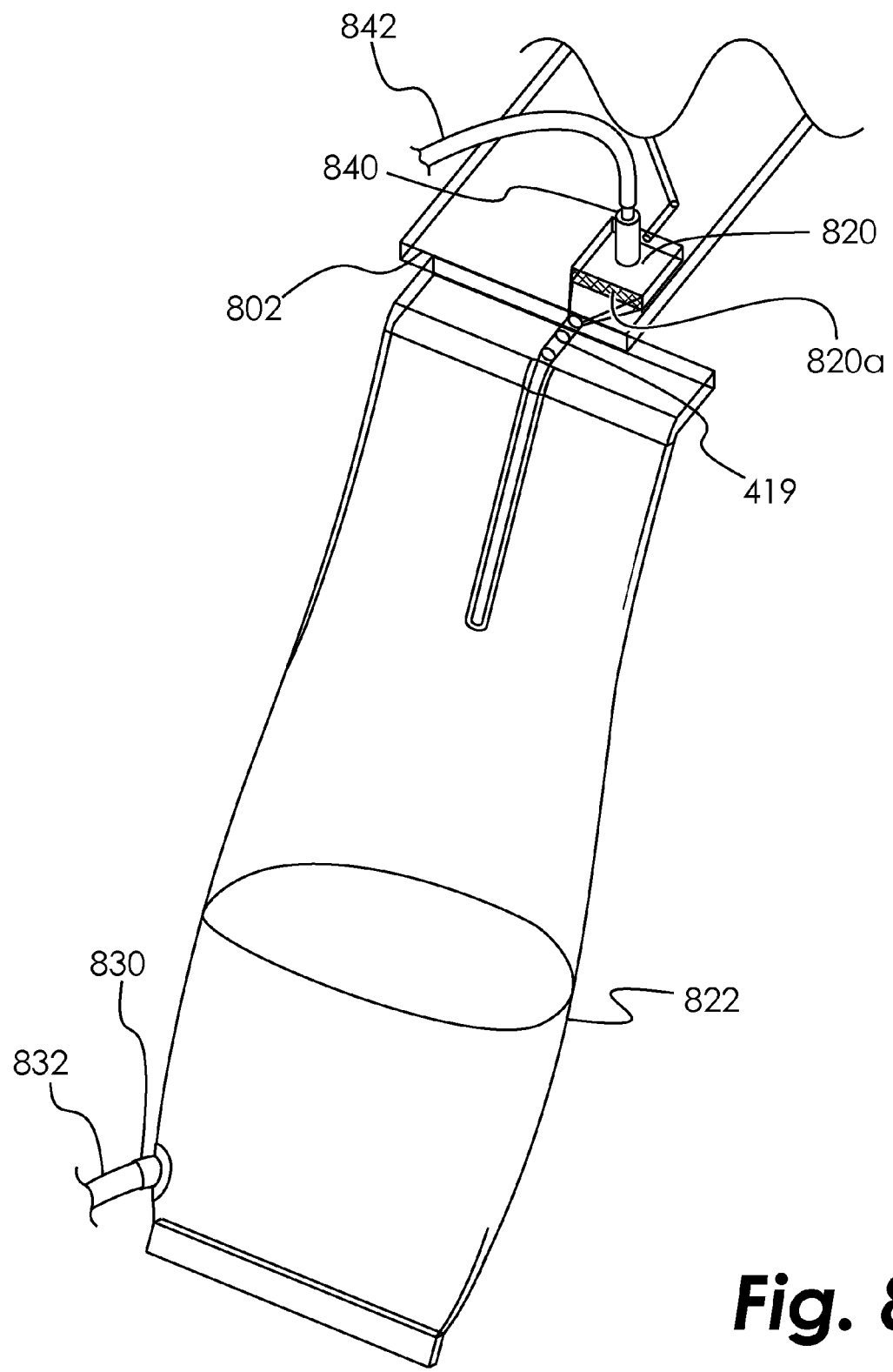
FIG. 8 is a schematic perspective view of a microfluidic device according to an embodiment of the present disclosure.

In certain embodiments, the present disclosure is generally directed to a system for the collection of cells, the collection system having an introduction port for the introduction of nutrients or other material and a waste port to remove waste from the collection system. The collection system may involve a single sterile collection bag, a dual chamber collection bag, a chamber or a well on a microfluidic device, such as a cytometry chip, the cells being diverted or directed into the collection system component following the cytometry analysis. In certain embodiments, the cytometry analysis is a flow cytometry analysis or an image cytometry analysis. FIG. 7 illustrates a microfluidic device 700 and FIG. 8 illustrates a microfluidic device 800. Except as discussed hereinbelow, the devices 700 and 800 are substantially similar to the device 400 of FIG. 4, and like reference designators are used to indicate like components.

FIG. 7 illustrates a microfluidic device 700 in which cells from a cell supply (not shown) are analyzed on the microfluidic device 700 via cytometry in analysis section 412 (the specific operations that occur in analysis section 412 are not critical to the present disclosure). According to the results of the analysis performed, the cells may be sorted into at least one well or chamber 414 and/or at least one sterile collection bag 716. In the illustrated embodiment, bag 716 is a dual chamber collection bag. However, it should be appreciated that the collection bag used in accordance with the collection system of this embodiment could be a single chamber collection bag. The cells collected in the dual chamber bag 716 may be, for example, stored and preserved within the bag for later viewing, imaging or testing by a researcher or medical professional and/or may be transported to a different location or delivered to a different process via the collection bag. Additionally, the bag 716 includes an introduction port 740 for the introduction of nutrients, reagents and/or other chemicals into the bag and a waste port 730 to remove waste from the bag.

In the illustrated example, after the cells are analyzed in analysis section 412, the cells may be sorted into either chamber 414 or dual chamber bag 716 based on differing characteristics of the cells. Cells may be sorted into the chamber 414 or the bag 716 based on the intended future use for the cells. For example, cells having the same characteristics, or phenotype, may be sorted into the chamber 414 where they are fixed for viewing and sorted into the bag 716 where they are maintained in a viable state to undergo additional functional measurements. Alternatively, the cells may be deposited into the chamber 414 and/or the bag 716 based on volume as opposed to a sorting method. For simplicity and ease of illustration, FIG. 7 shows single channels extending between the components, areas or sections of chip 700. However, it should be appreciated that the single channels may be representative of multiple cytometry channels and a variety of possible configurations of channels as would occur to one skilled in the art.

As illustrated, dual chamber bag 716 is composed of an inner porous bag 720 surrounded by an outer non-porous bag 722 substantially as described hereinabove with respect to bags 420, 422 of FIG. 4. In certain embodiments, the inner porous bag 720 serves as a filter for the material entering the dual chamber bag 716. In this way, the alive and functional cells sorted into bag 716 will remain in the inner porous bag 720, while debris such as dead or damaged cells will filter out into outer bag 722 via the porous nature of inner bag 720. Additionally, some, most, or all of the fluid material traveling with the cells will also filter through inner bag 720 into outer bag 722. The filtering of the fluid material may serve to wash the cells and further assist in transferring debris from the inner bag 720 into the outer bag 722. Additionally, the filtering of the fluid material may also serve to provide a higher concentrate of cells within inner bag 720. Higher concentrations of cells can be important in maintaining the integrity and functionality of the cells.

Dual chamber bag 716 may provide nutrients, reagents, and/or other chemicals to the cells sorted into inner bag 720 to feed the cells, keeping them alive and functional, and/or to fix the cells in the bag 720 in their current state for an extended period of time to maintain the integrity of the cell sample for later observation or testing by a medical professional. In such a way, the cells' morphology remains substantially in the same state as when they were sorted. This procedure maintains the integrity of the sorted and isolated cells, substantially preventing the cells from breaking down and thus preserving the morphological characteristic(s) of the cells which may have dictated their sorting. In some embodiments, the nutrients, reagents and/or other chemicals maintain the cells in a natural, viable state so that they can be placed in culture or used for additional functional measurements. In some embodiments, the nutrients, reagents and/or other chemicals in the bag 716 may facilitate preparation of the cells for freezing, such as by freezing the bag 716 by placing the bag in an automated cell cryogenic device, as an example.

According to the presently disclosed system, the nutrients, reagents, and/or other chemicals are delivered to bag 716 via introduction port 740. As illustrated, tube 742 couples with the introduction port 740 to deliver the materials to the bag 716. The introduction port 740 can be configured so that the materials are delivered to the inner bag 720 or the outer bag 722 as would occur to one of ordinary skill in the art. Additionally, system 700 includes an optional waste port 730 from bag 716, with tube 732 configured to couple with the waste port to remove debris material from the bag. In such a way, the debris and other waste material that filters through inner porous bag 720 and collects in outer bag 722 may be removed from the bag 716 via waste port 730. It should be appreciated that the introduction of nutrients, reagents and/or other chemicals through introduction port 740 can occur continuously or at intermittent times as would occur to one of ordinary skill in the art. It should be also appreciated that the removal of waste material through waste port 730 can occur continuously or at intermittent times as would occur to one of ordinary skill in the art.

FIG. 8 illustrates another collection system 800 according to another embodiment. System 800 is similar to system 700, with the function of inner porous bag 720 being replaced by a chamber or well 820 disposed onboard substrate 802. Accordingly, cells are analyzed via a cytometry analysis, such as flow cytometry or image cytometry, and sorted into well 820. In certain embodiments, well 820 includes a porous or filtering bottom surface 820a so that debris and other waste material passes through well 820 into waste collection bag 822, similar in function to outer bag 722 of system 700.

According to the presently disclosed system, nutrients, reagents, and/or other chemicals may be delivered into well 820 via introduction port 840. As illustrated, tube 842 couples to the introduction port 840 to deliver the materials to the well 820. In an alternative embodiment, the introduction port 840 can be coupled with collection bag 822, with the materials being delivered to bag 822. Additionally, system 800 includes a waste port 830 from bag 822, with tube 832 configured to couple to the waste port 830 to remove debris material from the bag. In such a way, the debris and other waste material that filters through bottom surface 820a of well 820 and collects in bag 822 may be removed from the bag 822 via waste port 830. It should be appreciated that the introduction of nutrients, reagents and/or other chemicals through the introduction port 840 and/or the removal of waste material through the waste port 830 can occur continuously or at intermittent times as would occur to one of ordinary skill in the art.

Figure 9:
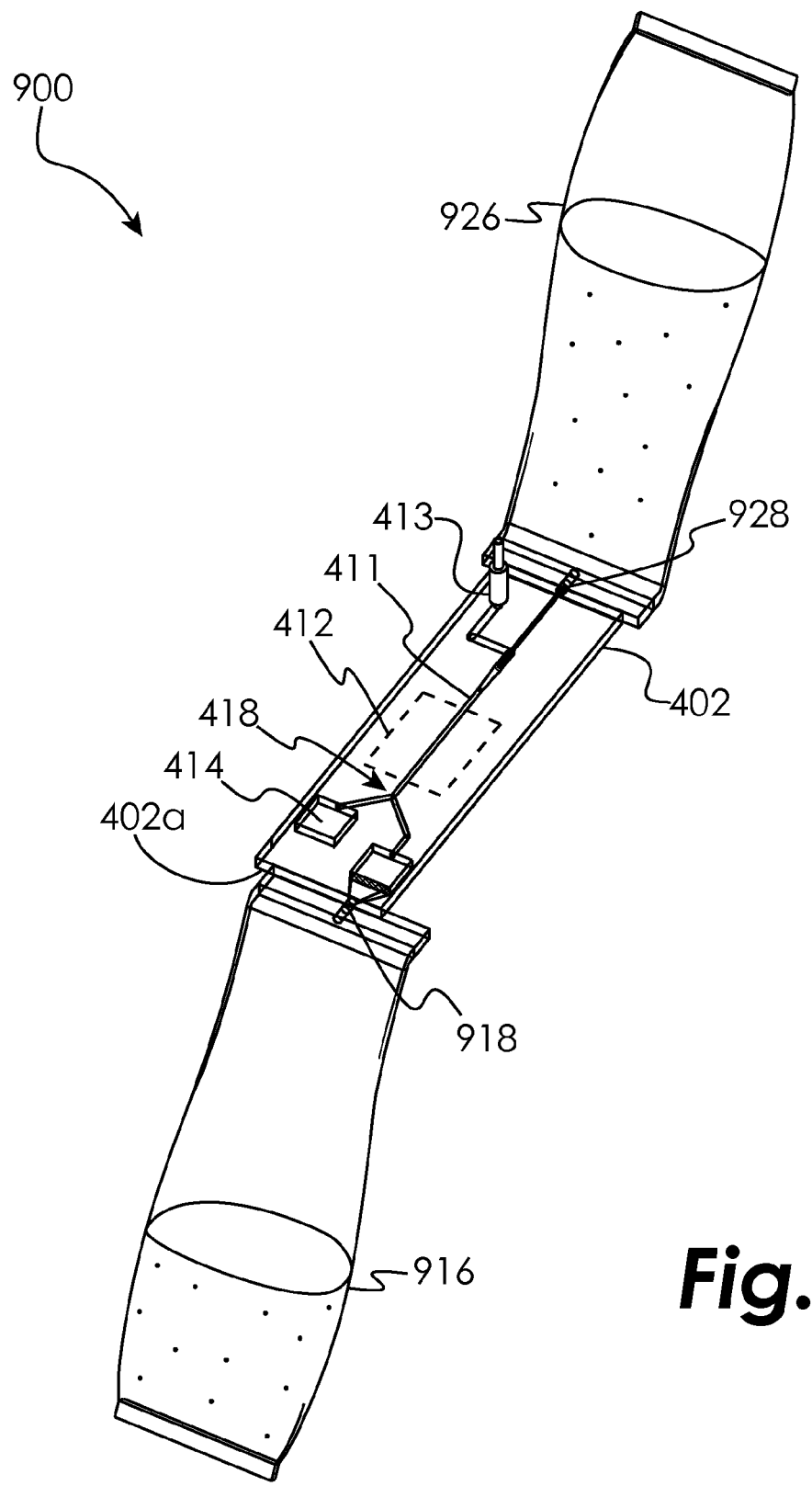
FIG. 9 is a schematic perspective view of a microfluidic device according to an embodiment of the present disclosure.

Microfluidic Device Having a Collection Bag Suitable for Use as an Introduction Bag In certain embodiments, the present disclosure is generally directed to a cytometry system having one or more collection bags suitable for the collection and introduction of cells with respect to a cytometry analysis occurring in conjunction with a microfluidic device, such as a cytometry chip. The bags may provide for the collection of cells following the cytometry analysis as well as the introduction of cells into the cytometry analysis. In certain embodiments, the cytometry analysis is a flow cytometry analysis or an image cytometry analysis. FIG. 9 illustrates a microfluidic device 900. Except as discussed hereinbelow, the device 900 is substantially similar to the device 400 of FIG. 4, and like reference designators are used to indicate like components.

FIG. 9 illustrates a system 900 in which cells from a cell supply contained within a collection bag 926 (serving as an introduction bag) are introduced onto the substrate 402 and analyzed via cytometry in analysis section 412 (the specific operations that occur in analysis section 412 are not critical to the present disclosure). According to the results of the analysis performed, the cells may be sorted into at least one well or chamber 414 and/or at least one sterile collection bag 916. The cells collected in the bag 916 may be, for example, stored and preserved within the bag 916 for later viewing, imaging or testing by a researcher or medical professional, transported to a different location, delivered to a different process via the collection bag, and/or introduced into an additional cytometry analysis occurring with respect to the same or another microfluidic device.

In the illustrated example, after the cells are analyzed in analysis section 412, the cells may be sorted into either chamber 414 or bag 916 based on differing characteristics of the cells. Cells may be sorted into the chamber 414 or the bag 916 based on the intended future use for the cells. For example, cells having the same characteristics, or phenotype, may be sorted into the chamber 414 where they are fixed for viewing and sorted into the bag 916 where they are maintained in a viable state to undergo additional functional measurements. Alternatively, the cells may be deposited into the chamber 414 and/or the bag 916 based on volume as opposed to a sorting method. For simplicity and ease of illustration, FIG. 9 shows single channels extending between the components, areas or sections of chip 900. However, it should be appreciated that the single channels may be representative of multiple cytometry channels and a variety of possible configurations of channels as would occur to one skilled in the art.

In certain embodiments, bags 916 and 926 may be identical or substantially identical collection bags. Additionally, in some embodiments each bag 916 and 926 is suitable for use as both or either a collection bag and an introduction bag. As an example, bag 916 may be detached from substrate 402 and used as an introduction bag, similar to bag 926, to introduce the cells collected within bag 916 (or another cell sample) into another cytometry analysis on another microfluidic device or onto cytometry chip 900. As another example, bag 926 delivering cells into analysis section 412 on chip 900 may have previously collected the cells contained therein from another process. As another example, bag 926 delivering cells into analysis section 412 on chip 900 may have previously collected different cells from another cytometry process, delivered those different cells to a location, and accepted the present cell sample for introduction onto chip 900. In alternative embodiments, the bags 916 and 926 are deposable after a single use such that once the bags either collect a cell sample or deliver a cell sample, the bags may be discarded.

Bags 916 and/or 926 may provide nutrients, reagents, and/or other chemicals to the cells contained therein to feed the cells, keeping them alive and functional, and/or to fix the cells in the bag in their current state for an extended period of time to maintain the integrity of the cell sample for later observation or testing by a medical professional. In some embodiments, the nutrients, reagents and/or other chemicals in the particular collection bag may facilitate preparation of the cells for freezing.

As in the illustrated embodiment, bags 916 and/or 926 may be removably attached to the substrate 402 via connection ports or members 918 and 928, respectively. In other embodiments, the bags 916 and/or 926 may removably attach directly to the cytometry channels on the substrate 402. For simplicity, the illustration of FIG. 9 shows one chamber 414, one collection bag 916 and one introduction bag 926; however, it should be appreciated that the microfluidic device may include more chambers 414, collection bags 916 and/or introduction bags 926 as would occur to one of ordinary skill in the art. Additionally, the chamber 414, collection bag 916 and/or introduction bag 926 may be positioned elsewhere on substrate 402 than as illustrated in FIG. 9 as would occur to one of ordinary skill in the art. Further, the bags 916 and 926 and chambers 414 may occupy a variety of a different shapes and sizes as would occur to one of ordinary skill in the art.

Figure 10:
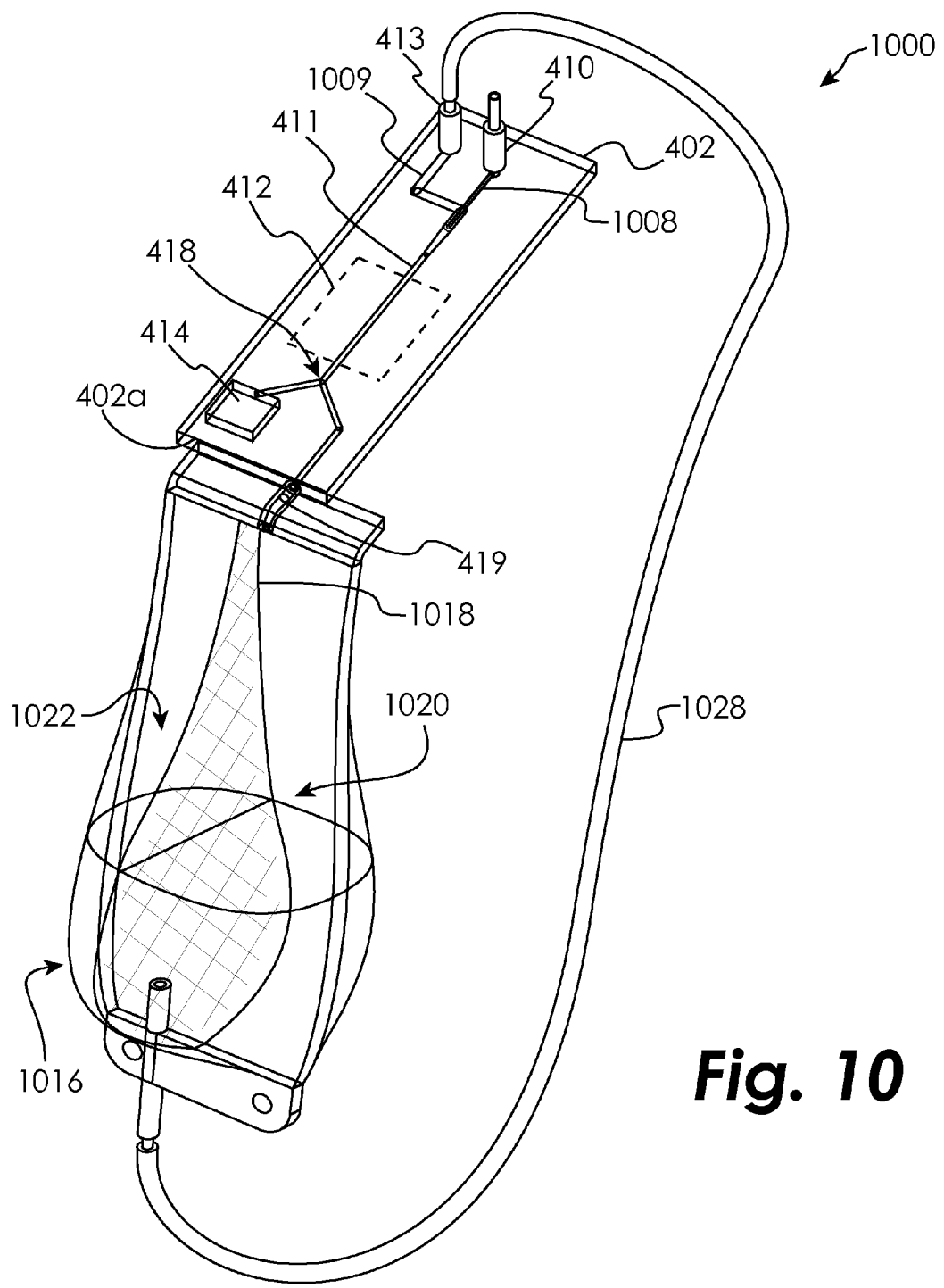
FIG. 10 is a schematic perspective view of a microfluidic device according to an embodiment of the present disclosure.

Microfluidic Device Having Sterile Collection Bag with Integral Sheath Fluid Supply In certain embodiments, the present disclosure is generally directed to systems for the collection of cells as well as the supply of sheath fluid via a sterile collection bag system on a microfluidic device. The bag system dually allows for the storage, preservation and transport of cells analyzed on a microfluidic device, such as a cytometry chip, as well as the supply of sheath fluid which can be introduced onto the microfluidic device and combined with the fluid sample to be analyzed to create a defined flow (such as a laminar flow) between the fluids. In certain embodiments, the cytometry analysis is a flow cytometry analysis or an image cytometry analysis. FIG. 10 illustrates a microfluidic device 1000. Except as discussed hereinbelow, the device 1000 is substantially similar to the device 400 of FIG. 4, and like reference designators are used to indicate like components.

FIG. 10 illustrates a system 1000 in which cells contained in a fluid sample from a cell supply (not shown) attached to input port 410, travel through a channel 1008 in substrate 402 and are combined with a sheath fluid supply in channel 1009, the sheath fluid being supplied from bag 1016. In certain embodiments, the fluid sample to be analyzed is introduced into the center or core of the sheath fluid to create laminar flow between the two different fluids and prevent build up along the walls of the cytometry channel by preventing the fluid sample from contacting the walls, as discussed hereinabove with respect to FIG. 1. The material is analyzed in the cytometry analysis section 412 (the specific operations that occur in analysis section 412 are not critical to the present disclosure). According to the results of the analysis performed, the cells in the sample/sheath fluid combination may be sorted into one or more different wells or chambers 414 and/or one or more different sterile collection bags 1016. The cells collected in the sterile collection bag 1016 may be, for example, stored and preserved within the bag for later viewing, imaging or testing by a researcher or medical professional and/or may be transported to a different location or delivered to a different process via the collection bag. For simplicity and ease of illustration, FIG. 10 shows single channels extending between the components, areas or sections of chip 1000. However, it should be appreciated that the single channels may be representative of multiple cytometry channels and a variety of possible configurations of channels as would occur to one skilled in the art.

As illustrated, bag 1016 is comprised of a collection compartment 1020 and a sheath fluid supply compartment 1022. In the illustrated example, after the cells are analyzed in analysis section 412, the cells may be sorted into either chamber 414 or collection compartment 1020 of sterile collection bag 1016 based on differing characteristics of the cells. Cells may be sorted into the chamber 414 or the bag 1016 based on the intended future use for the cells. For example, cells having the same characteristics, or phenotype, may be sorted into the chamber 414 where they are fixed for viewing and sorted into the bag 1016 where they are maintained in a viable state to undergo additional functional measurements or used for a cell-based therapeutic procedure. Alternatively, the cells may be deposited into the chamber 414 and/or the bag 1016 based on volume as opposed to a sorting method.

The collection bag 1016 is formed to have at least two compartments 1020 and 1022 by the presence of a divider wall 1018. The sheath fluid supply compartment 1022 of collection bag 1016 includes a supply of sheath fluid to be introduced into channel 1009 of chip 1000. In certain embodiments, a tube 1028 leads from compartment 1022 of bag 1016 to introduction port 413 which is in communication with channel 1009. Port 413 may be any appropriate fluid connection and introduction means as would occur to one of ordinary skill in the art. In other embodiments, tube 1028 leads directly into channel 1009 and thus port 413 is absent. The sheath supply may be caused to travel through tube 1028 in any appropriate manner as would occur to one skilled in the art, such as through the use of a pump (not shown). In certain embodiments, compartments 1020 and 1022 are not in fluid communication, such that commingling of the sorted and isolated cells collected in compartment 1020 and the sheath fluid supply in compartment 1022 does not occur. Accordingly, bag 1016 may be composed of a suitable non-porous material.

For simplicity, the illustration of FIG. 10 shows a single chamber 414 and a single bag 1016; however, it should be appreciated that the microfluidic device may include more chambers and/or bags as would occur to one of ordinary skill in the art. In an alternative embodiment, the microfluidic device may only include one or more sterile collection bags 1016, with the chamber 414 being absent. Additionally, the bag 1016 is shown as extending below the bottom surface 402a of the chip 1000; however, it should also be appreciated that the bag 1016 may be positioned elsewhere on the chip as would occur to one of ordinary skill in the art. Further, the bag 1016 may occupy a variety of a different shapes and sizes as would occur to one of ordinary skill in the art, with the bag 1016 illustrated in FIG. 10 being just one non-limiting example of the numerous possible shapes and sizes.

As in the illustrated embodiment, bag 1016 may be removably attached to the chip 1000 via connection port, tube or member 419. Connection member 419 may be any appropriate connection means as would occur to one of ordinary skill in the art. Connection member 419 communicates only with compartment 1020 and not compartment 1022. In other embodiments, the bag 1016 removably attaches directly to a flow channel leading from analysis section 412 and thus connection member 419 is absent. Once the analysis at section 412 is complete and the cells have been sorted into either the chamber 414 or the compartment 1020 of bag 1016, the entire bag 1016 or just compartment 1020 (for example, by making the dividing wall 1018 composed of two layers that may be separated) may be detached from chip 1000 to transport the cells or may remain attached to the chip 1000, either temporarily, semi-permanently or permanently, to store the cells for later imaging, viewing, transporting, processing, analysis or other intended use of the cells. In situations in which the cells are transported via the bag 1016 (or compartment 1020 thereof), the cells may be transported to a storage location or another process or analysis location, as examples.

In some embodiments, the collection compartment 1020 of the bag 1016 may contain the necessary nutrients, reagents and/or other chemicals therein to fix the cells in the bag 1016 in their current state, and keep them alive and functional, for an extended period of time to maintain the integrity of the cell sample for later observation or testing by a researcher or medical professional. In such a way, the cells' visual appearance or morphology remains substantially in the same state as when they were sorted. This procedure maintains the integrity of the sorted and isolated cells, substantially preventing the cells from breaking down and thus preserving the morphological characteristic(s) of the cells which may have dictated their sorting. In some embodiments, the nutrients, reagents and/or other chemicals maintain the cells in a natural, viable state so that they can be placed in culture or used for additional functional measurements or used for a cell-based therapeutic procedure. In some embodiments, the nutrients, reagents and/or other chemicals in the collection compartment 1020 of the bag 1016 may facilitate preparation of the cells for freezing, such as by freezing the bag 1016 (or compartment 1020) by placing the bag in an automated cell cryogenic device, as an example.

Additionally, in lieu of or in addition to the placement of nutrients, reagents and/or other chemicals in compartment 1020, the sheath fluid supplied in compartment 1022 of bag 1016 may contain nutrients, reagents and/or other chemicals to benefit the cells in the fluid sample. In certain embodiments, one or both compartments of the bag 1016 may be prepackaged with the necessary nutrients, reagents and/or chemicals therein.

Microfluidic Device Having Sheath Flow to Prevent Build-Up of Proteins

In certain embodiments, the present disclosure is generally directed to microfluidic devices, such as cytometry chips, which provide for a defined flow (such as a laminar flow) of sheath fluid surrounding a fluid sample through the cytometry channels of the device before, during and after the cytometry analysis. The cytometry analysis may be flow or image cytometry, as non-limiting examples. The sheath fluid surrounds the fluid sample throughout the device, including at channel transitions, by maintaining the defined flow between the two different fluids and preventing or reducing turbulence. As such, the sheath fluid is in contact with the inner walls of the cytometry channels to reduce build-up along the walls of protein or other resistance-causing substances.

Figure 11:
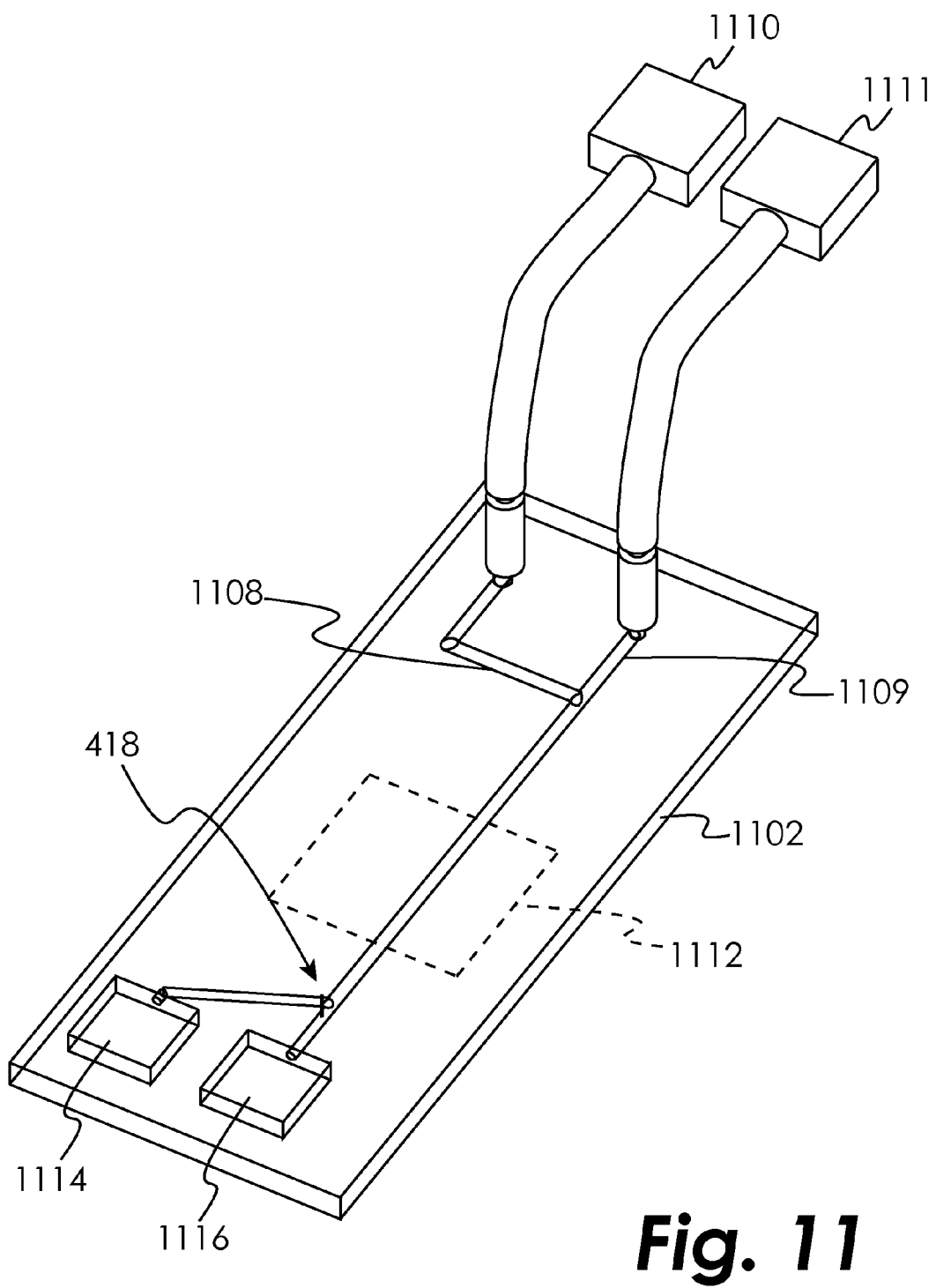
FIG. 11 is a schematic perspective view of a microfluidic device according to an embodiment of the present disclosure.
Figure 12:
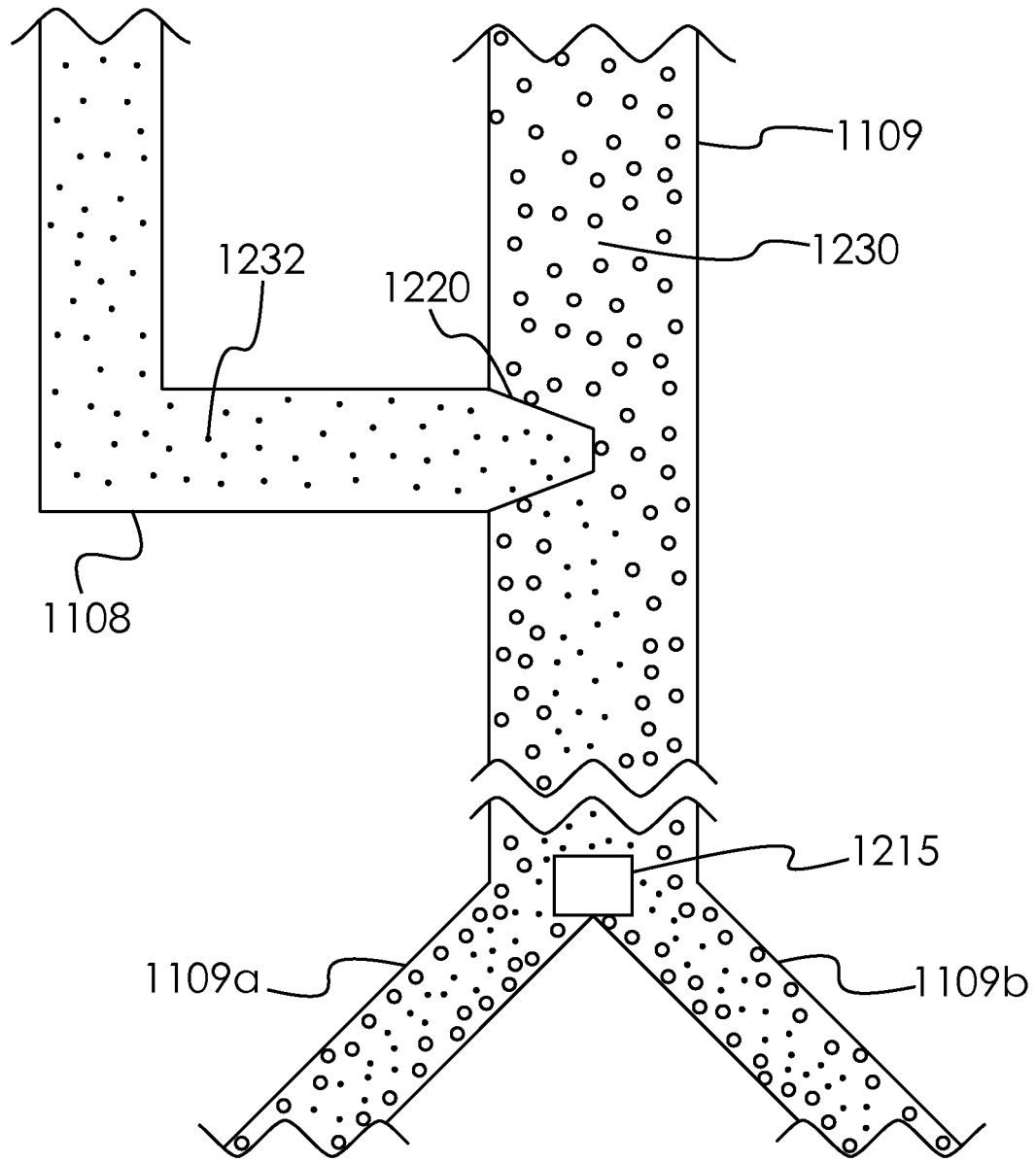
FIG. 12 is a schematic close-up cross-sectional view of the microfluidic device of FIG. 11.

FIGS. 11 and 12 illustrate a system 1100 for providing and maintaining a defined flow between a sheath fluid surrounding a fluid sample throughout a cytometry process. In certain embodiments, the material to be analyzed via the cytometry process are cells in a fluid originating from sample supply 1110. As generally shown in FIG. 11, the sample fluid travels through channel 1108 formed in substrate 1102 and joins sheath fluid originating from sheath supply 1111 in channel 1109. Thereafter the sample fluid is analyzed in the cytometry analysis section 1112 (the specific operations that occur in analysis section 1112 are not critical to the present disclosure).

According to the results of the analysis performed, the cells in the fluid sample may optionally be sorted into different chambers 1114 and 1116 based on differing characteristics of the cells. Cells may be sorted into different wells or chambers 1114, 1116 based on the intended future use for the cells. For example, cells having the same characteristics, or phenotype, may be sorted into one well where they are fixed for viewing, and sorted into another well where they are maintained in a viable state to undergo additional functional measurements. Alternatively, the cells may be deposited into the wells or chambers 1114, 1116 based on volume as opposed to a sorting method. Alternatively, the cells may be caused to exit the chip 1100 after the analysis is complete. For simplicity and ease of illustration, FIG. 11 shows single channels extending between the components, areas or sections of chip 1100. However, it should be appreciated that the single channels may be representative of multiple cytometry channels and a variety of possible configurations of channels as would occur to one skilled in the art.

Referring to FIG. 12, the fluid sample 1232 travels through channel 1108 and enters channel 1109 via introduction port 1220. In certain embodiments, introduction port 1220 is an end section of channel 1108 which narrows in diameter to introduce a desired amount of fluid sample 1232 into the center or core of the sheath fluid 1230. However, it should be appreciated that the fluid sample 1232 may be introduced into the sheath fluid 1230 in other appropriate manners as would occur to one of ordinary skill in the art. As illustrated in FIG. 12, the sheath fluid 1230 travels through channel 1109 and is moved toward the walls of channel 1109 as a result of the introduction of fluid sample 1232. Accordingly, the sheath fluid 1230 and fluid sample 1232 are directed to flow in parallel layers, with little or no disruption between the layers, otherwise known as laminar flow.

To maintain the flow of the sheath fluid 1230 along the walls of channel 1109 to prevent build-up thereon, laminar flow is maintained throughout the channels of the chip 1100 and turbulent flow is minimized or avoided altogether. As such, laminar flow is maintained through channel transitions which occur on the chip 1100. As an example illustrated in FIG. 12, channel 1109 splits into channels 1109a and 1109b, with the sample/sheath fluid combination diverted between the channels by diverter 1215. In certain embodiments, diverter 1215 is a mechanism to divert fluid flow which imparts little or no turbulence on the flow to maintain the laminar flow between the two different fluids. As an example, the diverter 1215 may be a piezoelectric device operable to divert the sheath/sample flow combination without impacting the laminar flow and thus without imparting turbulence into the combination flow. A piezoelectric actuated member may be capable of substantially blocking the flow toward one of channels 1109a or 1109b to divert the flow. As another example, an air bubble may be inserted into the channel 1109 from a port on the side of the channel to extend into the interior of the channel and divert flow with little or no turbulence. In such embodiments, the surface of the air bubble extending into the channel 1109 essentially takes the place of the channel wall and thus moves the effective channel wall toward the center of the channel 1109. This can divert flow into a bifurcated channel segment, such as channel 1109a or 1109b, at a downstream location. As even another example, the wall of channel 1109 may have a deformable section that acts in the same manner as the air bubble to divert flow.

Maintaining laminar flow between the sheath fluid 1230 and the sample fluid 1232 can be important in many situations. As an example, in situations in which the sample fluid is blood, the protein in the blood may build up along the walls of the cytometry channel when the blood is in contact with the walls. Introducing the blood into the center or core of a sheath fluid and maintaining that laminar flow prevents or reduces contact between the blood and the walls of the cytometry channel. This procedure reduces build up on the cytometry channel walls, thereby reducing friction and resistance encountered along the walls of the cytometry channel. Such friction will tend to disrupt the laminar flow and may eventually lead to clogging of the channel 1109.

Microfluidic Device Incorporating Enzyme or Detergent to Keep Channels Clean

Certain embodiments of the present disclosure are generally directed to microfluidic devices which provide for the inclusion of enzymes or other appropriate detergent materials into the fluid sample (or the sheath fluid, if present) to clean the cytometry channels on the microfluidic devices and thus maintain smooth fluid flow in the channels. The cytometry analysis may be flow or image cytometry, as non-limiting examples.

Figure 13:
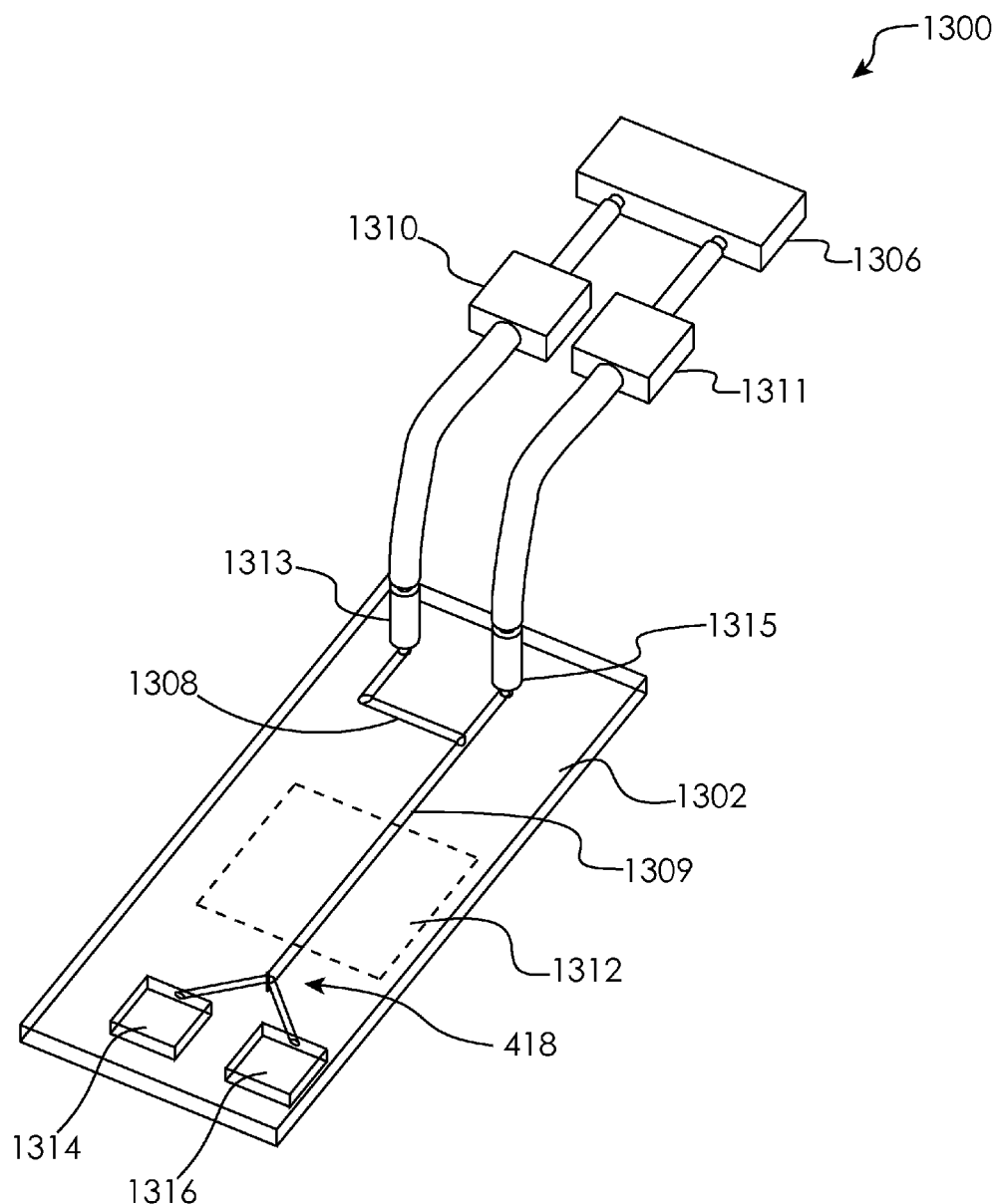
FIG. 13 is a schematic perspective view of a microfluidic device according to an embodiment of the present disclosure.

FIG. 13 illustrates a microfluidic device 1300 that allows for the introduction of enzymes or other appropriate detergent materials into the channels formed within a substrate 1302. In certain embodiments, the material to be analyzed via the cytometry process is cells in a fluid originating from cell sample 1310. Cells from cell sample 1310 are input to the substrate 1302 via input port 1313 which is fluidically coupled to flow channel 1308. In embodiments providing for sheath fluid, sheath fluid from supply 1311 is input to the substrate 1302 via the input port 1315 which is fluidically coupled to the flow channel 1309. The cell sample fluid 1310 travels through channel 1308 and joins sheath fluid 1311 in channel 1309. In other embodiments, the sheath fluid may be absent. Thereafter the sample fluid is analyzed in the cytometry analysis section 1312 (the specific operations that occur in analysis section 1312 are not critical to the present disclosure).

According to the results of the analysis performed, the cells in the sample material may optionally be sorted into different chambers 1314 and 1316 based on differing characteristics of the cells using flow diverter 418. Cells may be sorted into different wells or chambers 1314, 1316 based on the intended future use for the cells. For example, cells having the same characteristics, or phenotype, may be sorted into one well where they are fixed for viewing, and sorted into another well where they are maintained in a viable state to undergo additional functional measurements. Alternatively, the cells may be deposited into the wells or chambers 1314, 1316 based on volume as opposed to a sorting method. Alternatively, the cells may be caused to exit the substrate 1302 after the analysis is complete. For simplicity and ease of illustration, FIG. 13 shows single channels extending between the components, areas or sections of substrate 1302. However, it should be appreciated that the single channels may be representative of multiple cytometry channels and a variety of possible configurations of channels as would occur to one skilled in the art.

To assist in cleaning the channels on the substrate 1302, such as channels 1308 and 1309, and maintaining smooth fluid flow throughout the chip, one or more enzymes or other appropriate detergent materials 1306 may be introduced into one or both of the cell sample 1310 and sheath fluid 1311 prior to their entry into the cytometry channels. Enzymes lower the activation energy for a biological reaction and thus may dramatically increase the rate of the reaction. Accordingly, enzymes can be useful in detergents or other cleaning materials. Example enzymes used in detergents include proteases, amylases, lipases and cellulases. However, it should be appreciated that any appropriate enzyme or detergent material may be used to clean the inner walls of the cytometry channels. Although the schematic illustration of FIG. 13 shows the cell sample 1310 and sheath fluid 1311 receiving the enzyme or detergent material from a single source 1306, it should be appreciated that in certain embodiments, the cell sample 1310 and the sheath fluid 1311 may receive different enzyme or detergent materials, or may receive the same enzyme or detergent materials from separate sources.

In certain embodiments, the enzyme or detergent material 1306 assists in preventing the build-up of protein of other resistance-causing substances along the walls of the cytometry channels. As a particular example, in situations in which the sample fluid is blood, the protein in the blood may build up along the walls of the cytometry channel when the blood is in contact with the walls. Introducing the enzyme or detergent material 1306 into the blood sample and/or the sheath fluid reduces or eliminates the build-up of protein in the blood along the walls by cleaning the walls as the fluid moves through the cytometry channels. Reducing build up on the cytometry channel walls reduces the friction and resistance encountered by the sample fluid along the walls. Such friction will tend to disrupt the flow and may eventually lead to clogging of the channels.

With all of the embodiments disclosed herein, the use of a microfluidic device on a substrate offers many advantages, one of which is that the microfluidic device may be treated as a disposable part, allowing a new microfluidic device to be used for sorting each new sample of cells. This greatly simplifies the handling of the sorting equipment and reduces the complexity of cleaning the equipment to prevent cross contamination between sorting sessions, because much of the hardware through which the samples flow is simply disposed of. The microfluidic device also lends itself well to sterilization (such as by gamma irradiation) before being disposed of.

While the disclosure has been illustrated and described in detail in the drawings and foregoing description, the same is to be considered as illustrative and not restrictive in character, it being understood that only the preferred embodiments have been shown and described and that all changes and modifications that come within the spirit of the disclosure are desired to be protected.

What is claimed:

1. A microfluidic device, comprising:
a substrate;
an inlet port formed in said substrate;
a microfluidic flow channel having a first end and a second end, said flow channel formed in said substrate, said inlet port fluidically coupled to said flow channel at an intermediate position between said first end and said second end, wherein said flow channel extends through a portion of said substrate adapted to facilitate cytometry analysis of cells flowing in said flow channel;
a sterilization repository comprising a well formed in said substrate, said sterilization repository being fluidically coupled to said first end of said flow channel upstream from said inlet port; and
a substance disposed in said sterilization repository, said substance being operative to sterilize said flow channel when said substance flows from said sterilization repository into said flow channel.

2. The microfluidic device of claim 1, further comprising:
a valve disposed between said sterilization repository and said flow channel;
wherein fluid may flow from said sterilization repository to said flow channel when said valve is in an open position, and fluid is prevented from flowing from said sterilization repository to said flow channel when said valve is in a closed position.

3. The microfluidic device of claim 1, further comprising:
an input port fluidically coupled to said flow channel.

4. The microfluidic device of claim 3, further comprising:
a first sample well fluidically coupled to said flow channel;
a second sample well fluidically coupled to said flow channel; and
a flow diverter having a flow diverter input coupled to said flow channel, a first flow diverter outlet coupled to said first sample well, and a second flow diverter outlet coupled to said second sample well, said flow diverter having a first position and a second position;

wherein said flow diverter is operative to cause fluid in said flow channel to flow to said first sample well when said flow diverter is in a first position; and wherein said flow diverter is operative to cause fluid in said flow channel to flow to said second sample well when said flow diverter is in a second position.

5. The microfluidic device of claim 4, wherein said flow diverter is selected from the group consisting of: piezoelectric devices, air bubble insertion means, and magnetically actuated fluid deflectors.

6. The microfluidic device of claim 1, wherein a location of said sterilization repository is selected from the group consisting of: on said substrate and in said substrate.

7. The microfluidic device of claim 1, wherein said material is selected from the group consisting of: bleach and sodium hypochlorite.

8. The microfluidic device of claim 1, further comprising:
a cover affixed to said substrate and substantially sealing said well.

9. A method of detecting particles in a sample, the method comprising the steps of:
a) providing a microfluidic device, said microfluidic device comprising:
a substrate;
an inlet port formed in said substrate
a flow channel formed in said substrate for transport of a liquid sample, said flow channel having a first end and a second end, said inlet port fluidically coupled to said flow channel at an intermediate position between said first end and said second end;
a sterilization repository comprising a well formed in said substrate, said sterilization repository being fluidically coupled to said first end of said flow channel upstream of said inlet port;
a sterilizing substance disposed within said sterilization repository; and
a valve disposed between said sterilization repository and said flow channel;
b) flowing said sample through said flow channel to a portion of said substrate adapted to facilitate cytometry analysis of said particles in said sample; and
c) opening said valve such that said sterilizing substance contained in said sterilization repository may flow through said flow channel, thereby sterilizing said flow channel.

10. The method of claim 9, wherein said sterilizing substance is selected from the group consisting of: bleach and sodium hypochlorite.

* * * * *